United States Patent
Yonezawa et al.

(10) Patent No.: US 11,058,293 B2
(45) Date of Patent: Jul. 13, 2021

(54) IMAGE PROCESSING APPARATUS, OPHTHALMOLOGIC IMAGING APPARATUS, IMAGE PROCESSING METHOD, AND STORAGE MEDIUM

(71) Applicant: CANON KABUSHIKI KAISHA, Tokyo (JP)

(72) Inventors: Keiko Yonezawa, Kawasaki (JP); Kazuhide Miyata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 142 days.

(21) Appl. No.: 16/287,926

(22) Filed: Feb. 27, 2019

(65) Prior Publication Data

US 2019/0191987 A1    Jun. 27, 2019

Related U.S. Application Data

(63) Continuation of application No. 14/597,127, filed on Jan. 14, 2015, now abandoned, which is a continuation of application No. 13/605,873, filed on Sep. 6, 2012, now Pat. No. 8,960,906.

(30) Foreign Application Priority Data

Sep. 20, 2011   (JP) .................................. 2011-204653

(51) Int. Cl.
*A61B 3/14*     (2006.01)
*A61B 3/00*     (2006.01)
*G06T 7/00*     (2017.01)
*A61B 3/12*     (2006.01)

(52) U.S. Cl.
CPC .......... *A61B 3/0025* (2013.01); *A61B 3/0058* (2013.01); *A61B 3/1225* (2013.01); *A61B 3/14* (2013.01); *G06T 7/0012* (2013.01); *G06T 2207/10056* (2013.01); *G06T 2207/20056* (2013.01); *G06T 2207/30041* (2013.01)

(58) Field of Classification Search
None
See application file for complete search history.

(56) References Cited

U.S. PATENT DOCUMENTS

2010/0195048 A1 *   8/2010   Hammer ............... A61B 3/1025
                                                            351/206

FOREIGN PATENT DOCUMENTS

WO       WO03030073 A1 *   4/2003   ........... A61B 3/0025

\* cited by examiner

*Primary Examiner* — Mustak Choudhury
(74) *Attorney, Agent, or Firm* — Canon U.S.A., Inc. I.P. Division

(57) ABSTRACT

An image processing apparatus includes an identification unit configured to identify periodicity of a fundus image obtained by capturing an image of a fundus of an eye, and an information acquisition unit configured to acquire information indicating an imaging state of photoreceptor cells in the fundus image based on the periodicity.

19 Claims, 19 Drawing Sheets

IMAGE PROCESSING APPARATUS, OPHTHALMOLOGIC IMAGING APPARATUS, IMAGE PROCESSING METHOD, AND STORAGE MEDIUM

CROSS REFERENCE OF RELATED APPLICATIONS

This application is a continuation of U.S. patent application Ser. No. 14/597,127, filed on Jan. 14, 2015, which is a continuation of U.S. application Ser. No. 13/605,873, filed on Sep. 6, 2012 (now U.S. Pat. No. 8,960,906 issued on Feb. 24, 2015), which claims the benefit of Japanese Application No. 2011-204653, filed on Sep. 20, 2011, all of which is hereby incorporated by reference herein in their entirety.

BACKGROUND

Examination of a fundus of the eye is widely accepted as important in the early diagnosis of lifestyle-related diseases and diseases likely to cause blindness. Fundus cameras and scanning laser ophthalmoscopes (SLO) are among the apparatuses used for the inspection of the fundus of the eye. The fundus camera captures an image of a fundus of the eye by receiving reflected light of a light beam which has entered the fundus of the eye. The SLO is an ophthalmologic apparatus that uses the principle of confocal laser scanning microscope. In recent years, fundus cameras and SLOs including an adaptive optical system have been developed and are used for acquiring fundus planar images of high lateral resolution. The adaptive optical system measures an aberration of a subject's eye by a wavefront sensor in real time and corrects the aberration of the measuring beam and the return beam that occurs at the subject's eye by a wavefront correcting device. Further, attempts are being made to capture images of photoreceptor cells of a retina using by these apparatuses and make a diagnosis of a disease or evaluate drug response.

As an example of visualization of the photoreceptor cells using an adaptive optics SLO, Kaccie Y. Li and Austin Roorda, "Automated identification of cone photoreceptors in adaptive optics retinal images" J. Opt. Soc. Am. A, May 2007, Vol. 24, No. 5, 1358 discusses an ophthalmologic imaging apparatus which is capable of automated extraction of photoreceptor cells by acquiring a planar image of the fundus of the eye regarding the retina. According to this technique, a fundus planar image of a retina with high lateral resolution is acquired by preprocessing the acquired planar image, in other words, removing high frequency components from the planar image using periodicity of the arrangement of the photoreceptor cells visualized in the image.

SUMMARY

According to some embodiments of the present invention, an image processing apparatus includes an identification unit configured to identify periodicity of a fundus image obtained by capturing an image of a fundus of an eye, and an information acquisition unit configured to acquire information indicating an imaging state of photoreceptor cells in the fundus image based on the periodicity.

Further features and aspects of the present disclosure will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the embodiments of the present invention.

DESCRIPTION OF THE EMBODIMENTS

Figure 1:
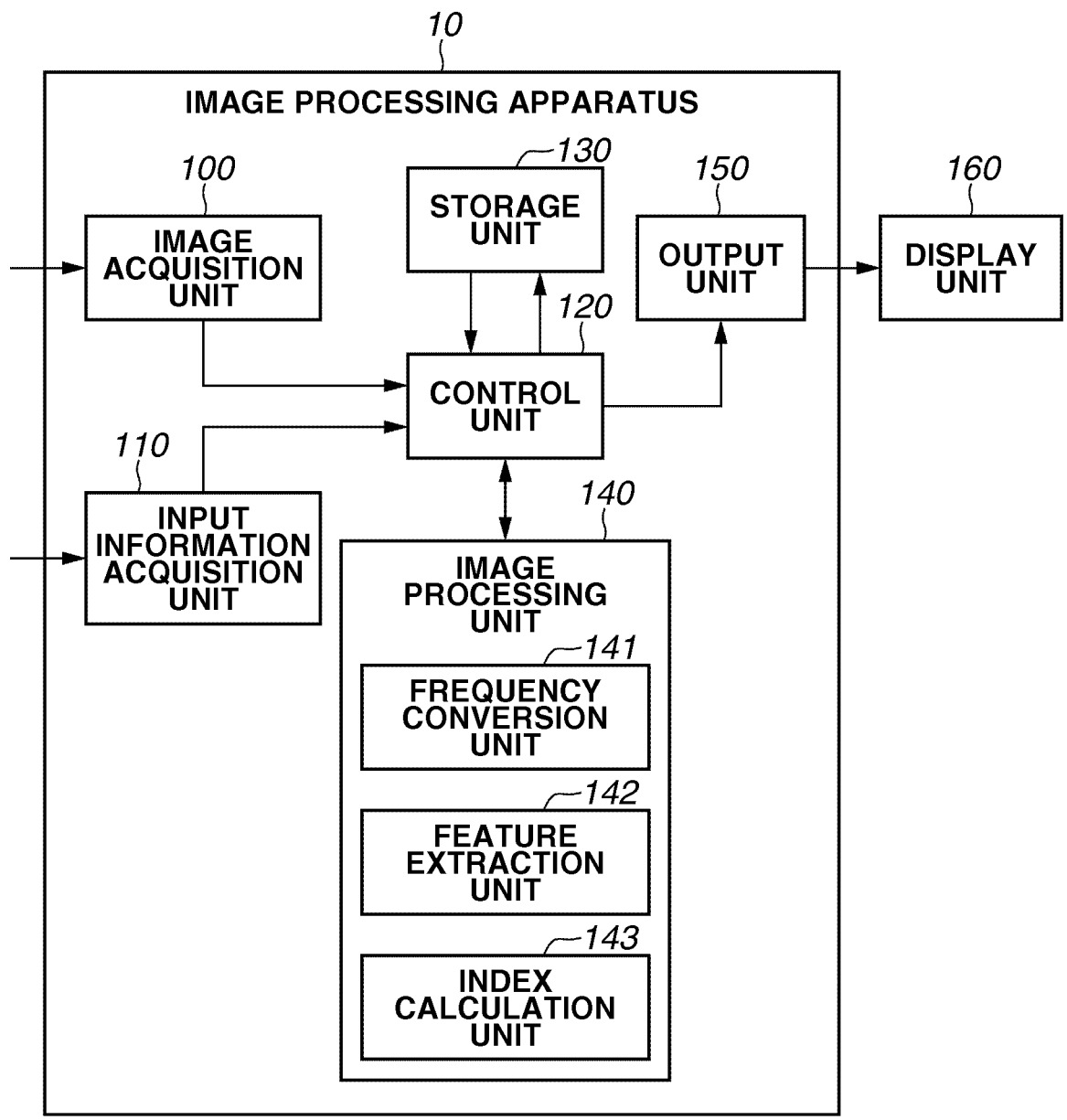
FIG. 1 illustrates a functional configuration of an image processing apparatus according to a first exemplary embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When images of photoreceptor cells are captured, it is useful to evaluate the imaging state of the image of the photoreceptor cells since such information helps the adjustment of the imaging conditions and the diagnosis of the obtained image. Generally, in evaluating an imaging state, an image quality index value is obtained according to a comparison of a noise level of a region being an evaluation target and a noise level of a different region. However, since the imaging area of the image of the photoreceptor cells is generally the retina region, the comparison method cannot be used for the evaluation.

In one embodiment of the present invention, an index that objectively evaluates an image quality of an image of photoreceptor cells of a retina acquired by an ophthalmologic apparatus such as an adaptive optics SLO is presented.

According to an exemplary embodiment of the present invention, since information of the imaging state of the photoreceptor cells can be obtained from processing of an image of the fundus of the eye, the adjustment of the imaging conditions and the diagnosis of the image can be easily performed.

According to a first exemplary embodiment, when an image is obtained by imaging of photoreceptor cells of a retina by an adaptive optics SLO, an index that quantitatively indicates the image quality of the acquired image is calculated and presented. More specifically, a spatial frequency image is acquired by discrete Fourier transform using a planar image of a fundus of the eye which has been acquired by the adaptive optics SLO. The acquired spatial frequency image is hereinafter referred to as a Fourier image or a frequency image. Then, a feature quantity of a periodic structure that reflects the regular arrangement of the photoreceptor cells is extracted from the acquired Fourier image, and the index of the image quality is acquired from the extracted feature quantity.

If the image quality index acquired in such a manner is presented when a user is capturing an image of the fundus of the subject's eye, the user can determine whether the image needs to be captured again. Further, if a diagnosis is to be performed based on the density of the photoreceptor cells, the user can determine whether it is adequate to use such an image for the diagnosis.

Figure 3:
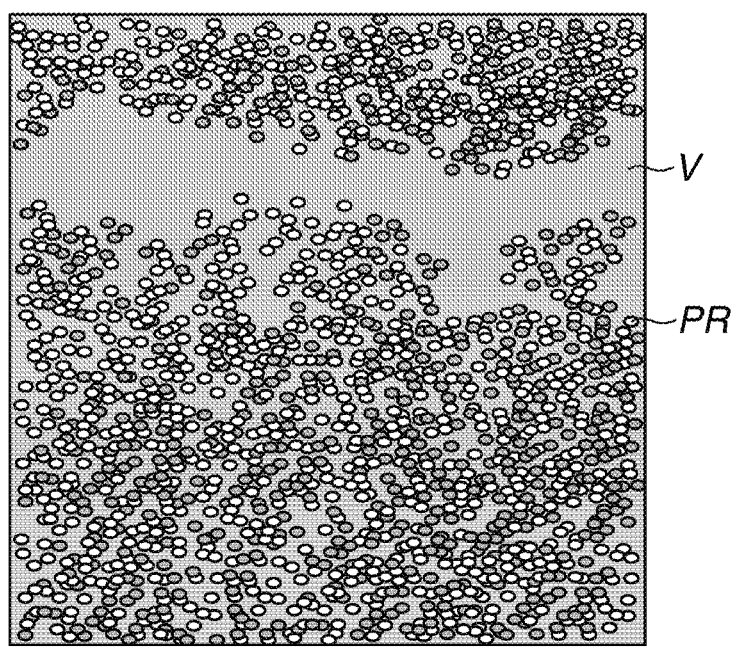
FIG. 3 is a schematic view of a high-precision planar image of a fundus of the eye including photoreceptor cells acquired by an adaptive optics SLO apparatus.

FIG. 3 schematically illustrates a planar image of the fundus of the eye captured by the adaptive optics SLO. As illustrated in FIG. 3, a small region having relatively high luminance can be extracted in a distinguishable manner as a photoreceptor cell PR. Further, a blood vessel region V having low luminance compared to the luminance of the photoreceptor cell may be extracted. The blood vessel region V is the shadow of the blood vessel above the photoreceptor cells.

Figure 4:
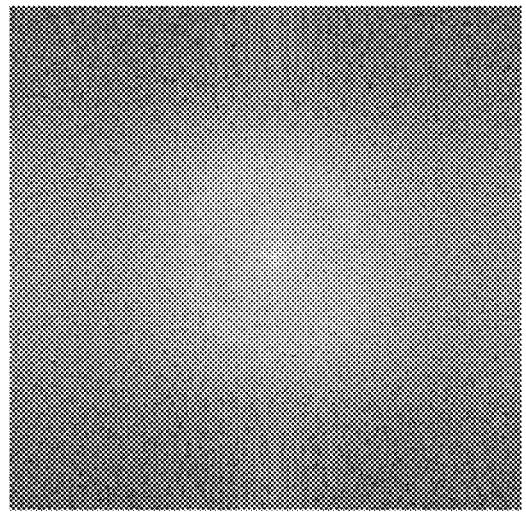
FIG. 4 illustrates an example of a Fourier image obtained by frequency conversion of the planar image of the fundus of the eye.

FIG. 4 illustrates an example of a Fourier image acquired by the discrete Fourier transform of spatial frequency components of the planar image of the fundus of the eye described above. As illustrated in FIG. 4, a ring that corresponds to the periodicity of the photoreceptor cells is formed according to the periodic arrangement of the photoreceptor cells.

FIG. 1 illustrates a functional configuration of an image processing apparatus 10 according to the present embodiment.

An image acquisition unit 100 in FIG. 1 acquires a planar image of a fundus of the eye. The acquired planar image is an image of photoreceptor cells of the fundus of the eye. For example, it is an image acquired by a fundus imaging apparatus which includes an aberration measurement unit such as a Hartmann-Shack wavefront sensor and an adaptive optical system which corrects the aberration. The adaptive optical system includes, for example, a reflective display panel having liquid crystals arranged on a silicon substrate (liquid crystal on silicon (LCOS)) or a deformable mirror.

When the planar image of the fundus of the eye is captured by the adaptive optics SLO, an input information acquisition unit 110 acquires information of the subject's eye which is being captured. The acquired image is stored in a storage unit 130 via a control unit 120. An image processing unit 140 includes a frequency conversion unit 141, a feature extraction unit 142, and an index calculation unit 143.

The frequency conversion unit 141 performs frequency conversion of the planar image of the fundus of the eye and obtains a frequency image. For example, the discrete Fourier transform is used for converting frequencies, as described above.

The feature extraction unit 142 extracts the feature quantity indicating the periodic structure of the planar image of the fundus of the eye from the frequency image. In the frequency image, the periodic structure of the planar image of the fundus of the eye is, for example, appears in a ring structure having a point of origin at the center. The ring of the frequency image presents a specified frequency band corresponding to the structure of the photoreceptor cells.

The feature quantity of the periodic structure is, for example, the feature quantity concerning this ring structure such as a peak luminance value in the ring structure and a sharpness value that indicates the extension of the ring structure. Further, there is the peak position of the luminance value in the ring structure. Additionally, if the image quality is poor, a disk-like structure may appear in the frequency image rather than the ring structure. In this case, the extension and the position of the disk region, and the peak luminance value in the disk region are extracted as the feature quantities. These are used for acquiring information of the imaging state and the distribution information of the photoreceptor cells in the planar image of the fundus of the eye.

The periodicity can be identified using information other than the frequency image. For example, the peak value of the luminance near the center of the photoreceptor cells is detected and an average of the profile of luminance distribution around each detection point is acquired. In this manner, the periodicity of the image of the fundus of the eye can be identified.

The peak value can be detected using maximum value detection processing. The profile in this context is in the radial direction having the detection point at the center, and the mean value is taken in the angular direction of the polar coordinates having the detection point at the center. Then, the feature extraction unit 142 evaluates the shape. If the shape is periodic, a peak corresponding to a detection point adjacent to the detection point appears on the average profile.

Additionally, as a method for identifying the periodicity, co-occurrence matrix and fractal dimension known as the texture feature quantity can be used.

The identification of the periodicity by the Fourier transform is one exemplary embodiment, and the above-described different methods can be used in identifying the periodicity. In this regard, the frequency conversion unit 141 functions as one exemplary embodiment of an identification unit of the periodicity.

The index calculation unit 143 functions as an information acquisition unit configured to acquire information of the imaging state of the photoreceptor cells and distribution information of the photoreceptor cells from the image indicating the periodicity such as a Fourier image. By using the feature quantity extracted by the feature extraction unit 142, the index calculation unit 143 can obtain accurate calculation results of the imaging state and the distribution of the photoreceptor cells.

An output unit 150 outputs the information of the imaging state and the distribution information of the photoreceptor cells acquired by the index calculation unit 143. The information is output to a display unit 160 as well as an external database and an output apparatus. The information is, for example, printed out by the output apparatus. Information of the imaging state can be displayed as it is or together with the planar image of the fundus of the eye on the output apparatus.

Figure 5A:
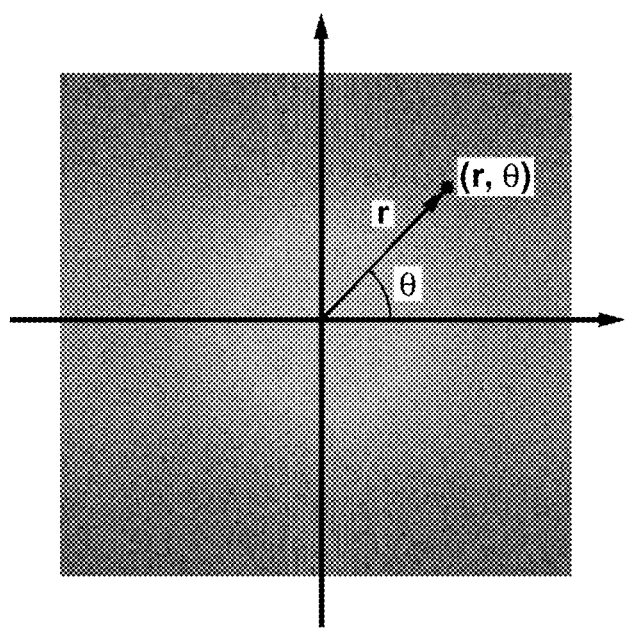
FIGS. 5A and 5B illustrate a method for calculating a structure that reflects an arrangement of the photoreceptor cells from a Fourier image and a graph organizing the result of the calculation.
Figure 5B:
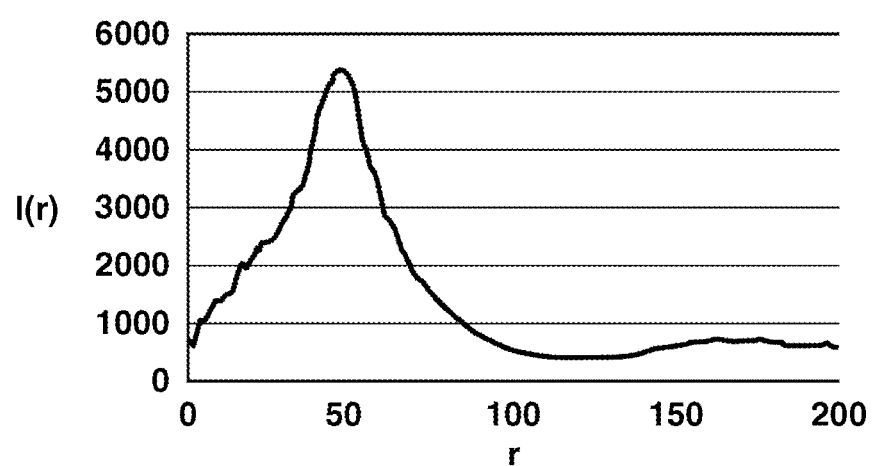

As the information of the imaging state which is displayed, there is the image quality index value of the planar image of the fundus of the eye where the photoreceptor cells have been captured, and information asking the user to perform operation to improve the imaging state. Further, a frequency image including the information of the imaging state can be displayed together with the image of the fundus of the eye. Furthermore, as illustrated in FIG. 5B described below, a graph showing a relation between a distance from the center position of the ring structure or from the point of origin of the frequency image and the luminance value is displayed. Additionally, a control value corresponding to the imaging state of the photoreceptor cells is output to the ophthalmologic imaging apparatus which has captured the planar image of the fundus of the eye.

The image processing unit 140 generates a Fourier image from the acquired planar image of the fundus of the eye, calculates an index of the image quality from the feature quantity extracted from the Fourier image, and stores the index in the storage unit 13. The output unit 150 outputs the calculated index to a monitor. Further, the output unit 150 outputs the result of the processing stored in the storage unit 130 to the database.

Although the image processing apparatus 10 acquires the planar image of the fundus of the eye directly from the adaptive optics SLO in the present embodiment, the image can be acquired via a network. In such a case, a plurality of planar images of the fundus of the eye captured by the adaptive optics SLO are stored in a database connected to the adaptive optics SLO via the network, and the image processing apparatus 10 acquires the images from the database via the network.

Figure 2:
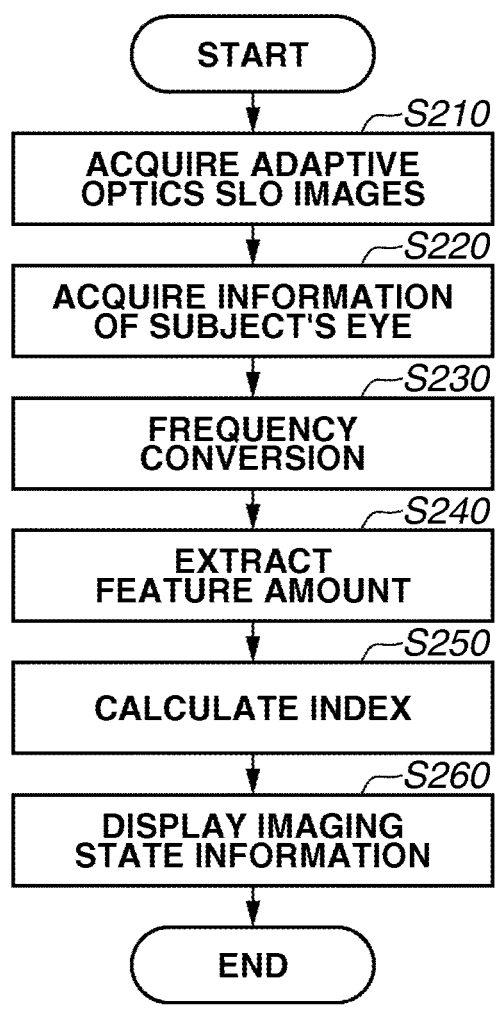
FIG. 2 is a flowchart illustrating processing procedures of the image processing apparatus according to the first exemplary embodiment.

Next, processing procedures of the image processing apparatus 10 according to the present embodiment will be described with reference to the flowchart of FIG. 2.

In step S210, the image acquisition unit 100 acquires a plurality of planar images of the fundus of the eye to be analyzed from the adaptive optics SLO connected to the image processing apparatus 10 or a database where the planar images of the fundus of the eye captured by the apparatus are stored. The acquired planar images of the fundus of the eye are stored in the storage unit 130 via the control unit 120.

Further, the image acquisition unit 100 acquires imaging parameter information of the planar images of the fundus of the eye when they are captured and stores the information in the storage unit 130 via the control unit 120. The imaging parameter information is, for example, position information of the fixation lamp when the imaging is performed. The imaging parameter information such as the position information of the fixation lamp may be included in an information file which is added to the planar images of the fundus of the eye, but may also exist as tag information of the images.

In step S220, the input information acquisition unit 110 acquires information of the subject's eye from the database or from the input of the operator via an input unit (not illustrated). The information of the subject's eye is information of the patient (e.g., patient ID, name, age, and sex), whether the examination target is right/left eye, and shooting date and time. The acquired information is stored in the storage unit 130 via the control unit 120.

In step S230, the frequency conversion unit 141 acquires a spatial frequency image by the discrete Fourier transform using the planar images of the fundus of the eye acquired by the adaptive optics SLO and stored in the storage unit 130. As illustrated in FIG. 3, a greater part of each planar image of the fundus of the eye is populated with regularly-arranged photoreceptor cells observed as small regions with high luminance. Thus, even if the image partially includes a blood vessel or a region of lesion, a Fourier image obtained from such a planar image of the fundus of the eye by spatial frequency conversion has a ring structure as illustrated in FIG. 4.

In step S240, the feature extraction unit 142 extracts a feature quantity of the ring structure that shows the periodicity of the arrangement of the photoreceptor cells from the Fourier image obtained in step S230. More specifically, as illustrated in FIG. 5A, if the Fourier image is a square image having a number N of pixels in the vertical and horizontal directions (i.e., a square of N×N pixels), polar coordinates (r, θ) having the center of the Fourier image (coordinates (N/2, N/2)) as the point of origin is considered. Then, a function I(r), which is obtained by calculating the value of each pixel of the Fourier image in the θ direction, is calculated where r=0, 1, 2 ... N/2. Since the Fourier image is not a continuous image and each pixel has a value, when the function I(r) is calculated, if r of each pixel is, for example, 4.5 or greater and smaller than 5.5, the value of I(5) is used. Subsequently, the function I(r) is smoothed, for example, by acquiring a mean value of adjacent points. FIG. 5B illustrates a function I(r) acquired from the Fourier image in FIG. 5A.

Figure 6A:
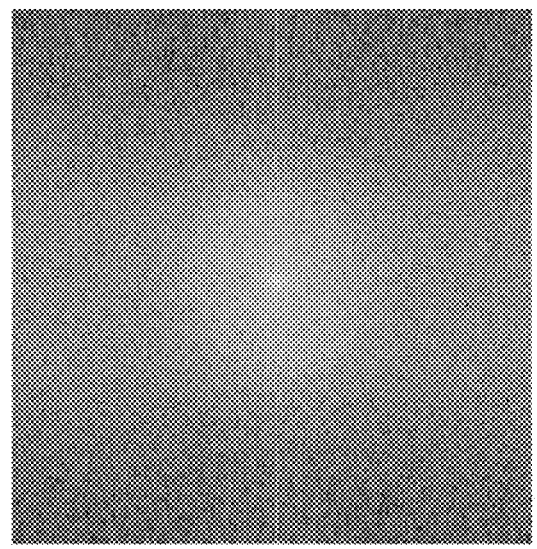
FIGS. 6A and 6B illustrate an example of a Fourier image obtained by frequency conversion of the planar image of the fundus of the eye in a case where the signal is weak and a graph indicating the arrangement of the photoreceptor cells.
Figure 6B:
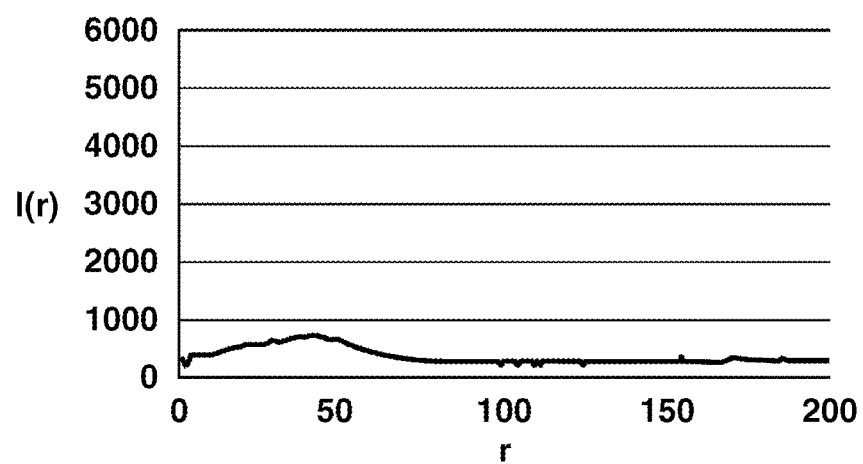
Figure 7:
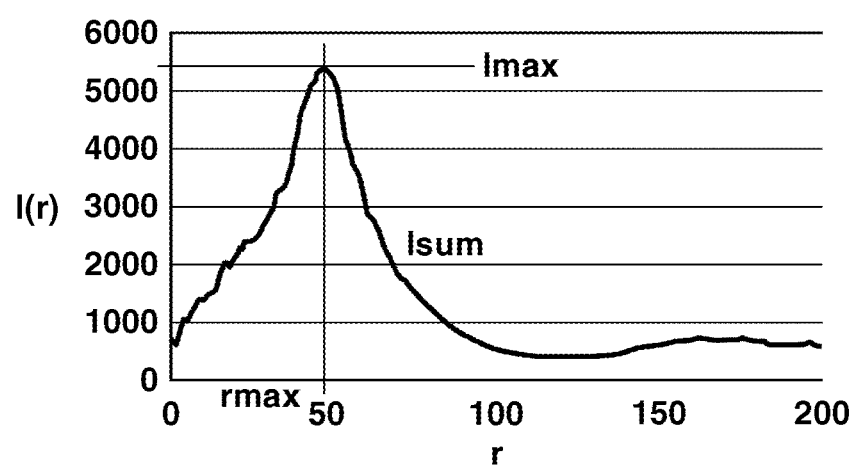
FIG. 7 illustrates a feature quantity acquired from a Fourier image.

The function I(r) in FIG. 5B includes a lot of information regarding the arrangement of the photoreceptor cells. For example, when the crystalline lens of the subject's eye becomes cloudy due to a disease, the signals of the photoreceptor cells become extremely weak (see FIG. 6A). In such a case, as illustrated in FIG. 6B, the value of the function I(r) itself becomes small compared to the function I(r) in FIG. 5B. Further, if the photoreceptor cells are partially absent in the imaging region and a periodic structure is not produced, a similar function I(r) is obtained. Thus, as a feature quantity indicating the intensity of the periodic structure of the photoreceptor cells, as illustrated in FIG. 7, Imax (i.e., a maximum value of I(r)) and Isum (i.e., a sum of I(r)) can be used.

$$I_{max} = \max_r I(r)$$

$$I_{sum} = \sum_r I(r)$$

Further, rmax, which is a value of r of Imax, corresponds to the periodicity of the arrangement of the photoreceptor cells.

$$r_{max} = \arg\max_r I(r)$$

If the distance between adjacent photoreceptor cells is small and the photoreceptor cells are densely arranged, rmax becomes greater. Conversely, if the photoreceptor cells are distant from the macula lutea and the density of the photoreceptor cells is low, rmax becomes smaller.

Figure 8A:
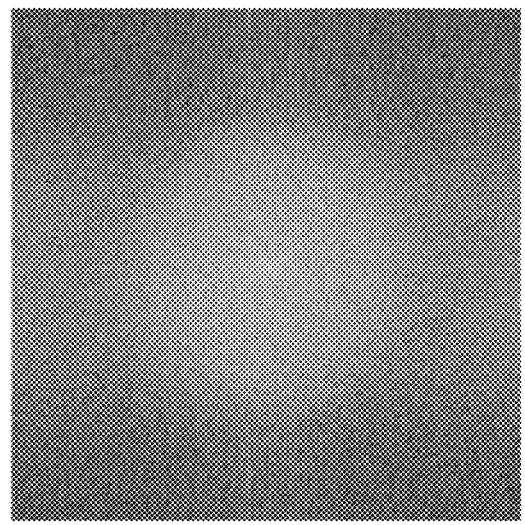
FIGS. 8A, 8B, and 8C illustrate an example of a Fourier image of low resolution and feature quantities acquired from the image.
Figure 8B:
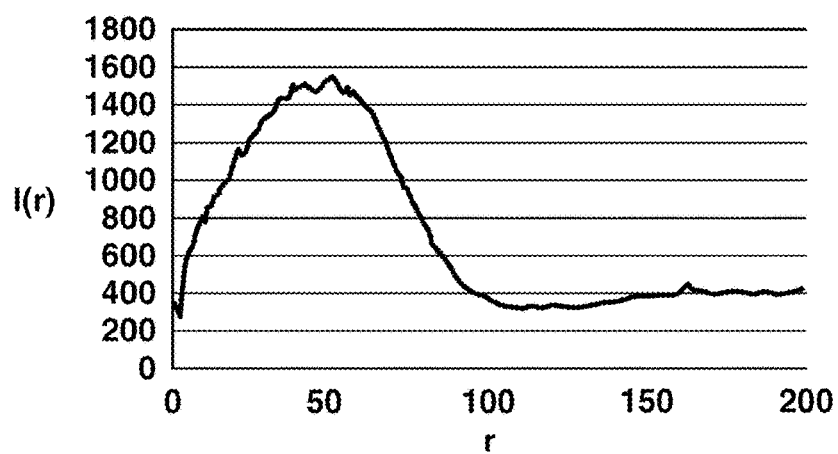
Figure 8C:
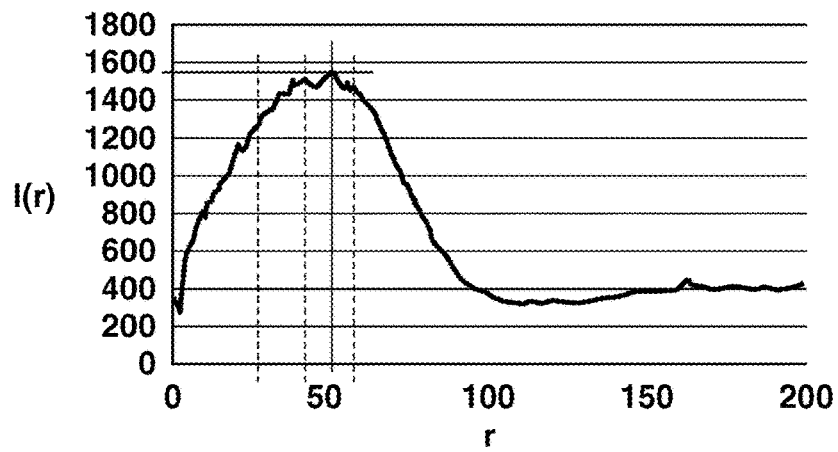

Further, even if the signal strength is strong enough, the periodic structure of the photoreceptor cells may not be clearly determined due to low resolution (see FIG. 8A). In such a case, as illustrated in FIG. 8B, the shape of the function I(r) is broadened toward the smaller function r. As a feature quantity that represents such poor resolution, a ratio of a sum of values around rmax (±n) and a sum of values around r smaller than rmax is calculated. FIG. 8C illustrates the calculation regions.

$$\text{peak\_ratio} = \frac{I_{sum\_peak}}{I_{sum\_low}} = \frac{\sum_{r=r_{max}-n}^{r_{max}+n} I(r)}{\sum_{r=r_{max}-3n}^{r_{max}-n} I(r)}$$

Figure 9A:
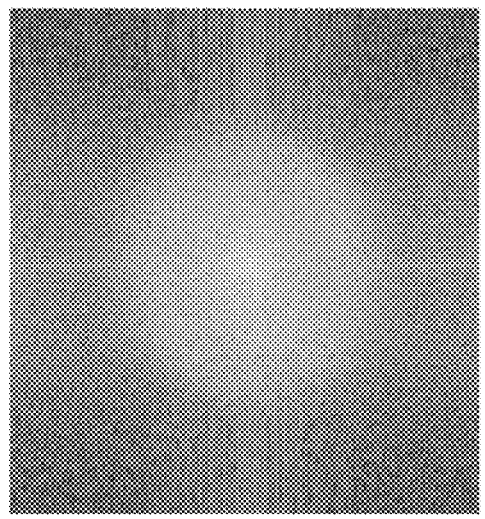
FIGS. 9A, 9B, and 9C illustrate an example of a Fourier image of even lower resolution and feature quantities acquired from the image.
Figure 9B:
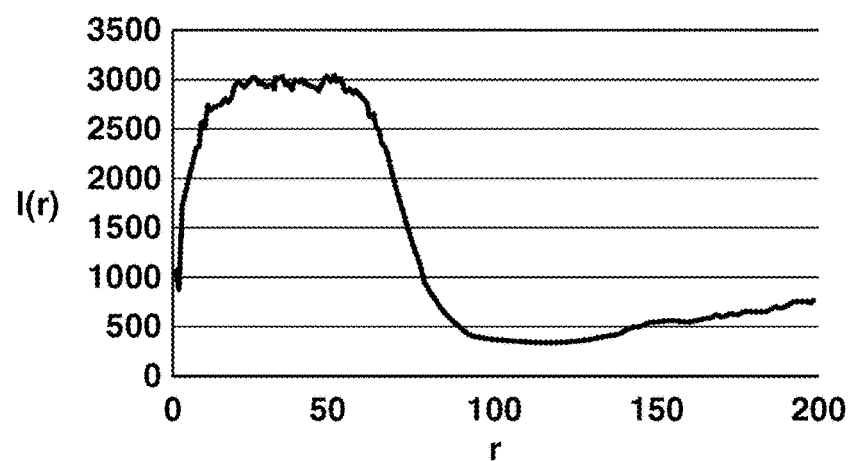
Figure 9C:
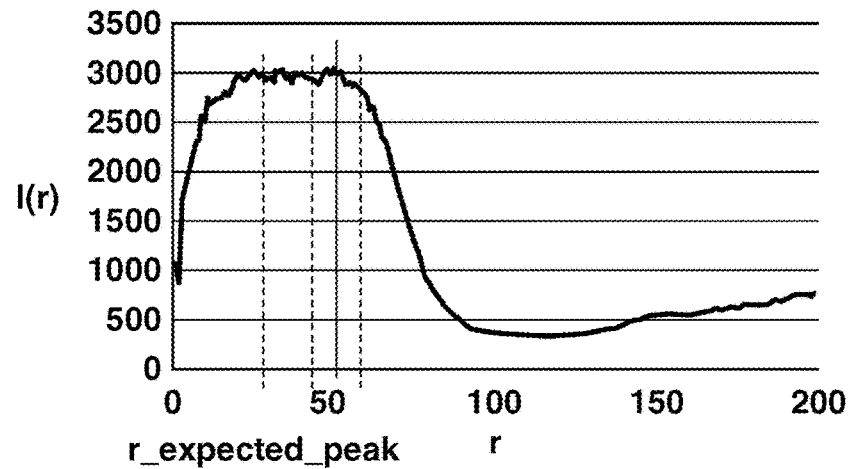

If the imaging condition is poor and the resolution is low (FIG. 9A), it may be difficult to acquire the peak I(r). FIG. 9B illustrates the signals of I(r) in such a case. In such a case, even if Imax is acquired, accurate peak_ratio cannot be calculated. In such a case, a peak position which is assumed from the acquired visual fixation information (position r_expected_peak) will be used in place of rmax in calculating the peak_ratio. In this manner, the resolution of the image can be evaluated more accurately.

In step S250, from the feature quantity acquired in step S240, the index calculation unit 143 acquires information of the photoreceptor cells such as the information of the imaging state and the distribution information of the photoreceptor cells of the image captured by the adaptive optics SLO. The acquired image quality index is stored in the storage unit 130 via the control unit 120. An example of a method for calculating the image quality index from the feature quantity acquired in step S240 will be described below. The index which is acquired, however, is not limited to the calculation method described below.

Among a plurality of indices extracted in step S240, the indices associated with the intensity of the periodic structure of the photoreceptor cell such as Imax and Isum and those associated with the resolution such as the peak_ratio are important in terms of image quality. Regarding the adaptive optics SLO, even if the health level of the subject's eye is good and high signal can be obtained, good resolution is not always obtained.

In such a case, an image of good quality may be acquired if, for example, the aberration is corrected again using the wavefront sensor. Thus, it is important to differentiate such an image from an image of a subject's eye with a cloudy crystalline lens less likely to produce good image. Thus, by combining the index associated with the intensity of the periodic structure and the index associated with the resolution in a two-dimensional manner, information which can more accurately present the imaging state can be acquired compared to a case where information is acquired from each index.

Figure 10A:
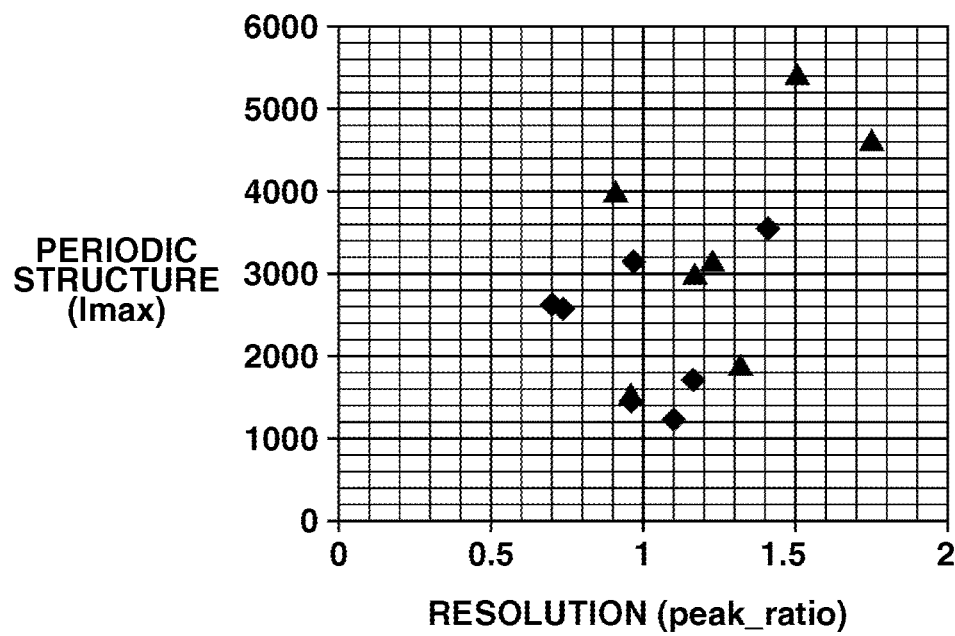
FIGS. 10A and 10B illustrate an image quality index acquired from a feature quantity (or feature amount) extracted from a Fourier image.
Figure 10B:
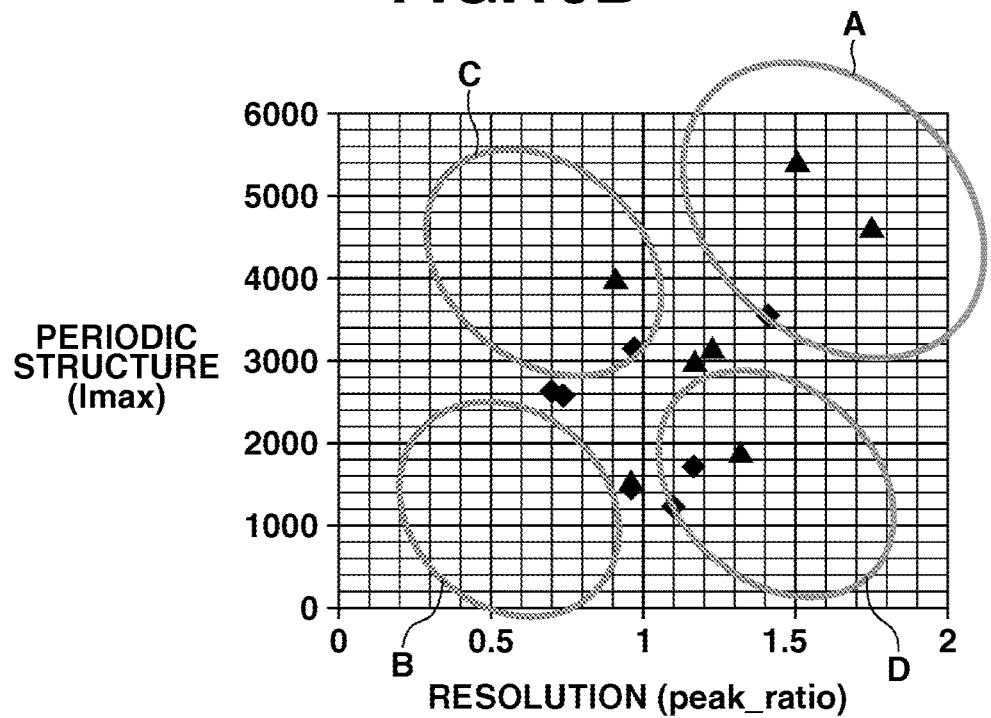

FIGS. 10A and 10B illustrate examples of an image quality index acquired from a feature quantity (or feature amount) extracted from a Fourier image (or frequency image). In FIGS. 10A and 10B, the vertical axis represents Imax, which is an index associated with the intensity of the periodic structure and the horizontal axis represents the peak_ratio, which is an index associated with the resolution. In step S240, a case where rmax is used for calculating the peak_ratio and another case where the position r_expected_peak is used for calculating the peak_ratio have been described. Generally, when the signal strength is reduced, the noise is increased, and it becomes difficult to acquire an accurate rmax. Thus, in FIGS. 10A and 10B, a case where the peak_ratio is calculated using the r_expected_peak is presented.

As illustrated in FIG. 10B, an image in a region A, which is a high index region regarding the intensity of the periodic structure and the resolution, is considered as an image of good quality. An image in a region B, which is a low index region regarding the intensity of the periodic structure and the resolution, is considered as an image of poor quality. Regarding an image in a region C, which is a high index region regarding the intensity of the periodic structure but a low index region regarding the resolution, the state of the subject's eye is not bad but the resolution may be poor. If such an image is acquired, by performing the aberration correction again, the image quality may be improved. Such an image may also include both a region where the structure of the photoreceptor cells is clear a region where the structure of the photoreceptor cells is not clear. Such a portion may correspond to a lesion portion. Further, an image in a region D, which is a low index region regarding the intensity of the periodic structure and a high index region regarding the resolution, has good resolution but weak signals in general. If an image is such, a clearer image may be acquired by increasing the signal strength.

In step S260, the output unit 150 acquires the information indicating the imaging state, such as the image quality index, stored in the storage unit in step S250 and displays it on the display unit 160.

For example, the acquired feature quantity is displayed as it is as the information of the imaging state. Although detailed information can be presented to the user, if a threshold value of the image quality index is set in advance when the image index value is smaller than the threshold value, a message such as "low image quality of photoreceptor cell region" can be displayed on the display unit 160 by the output unit 150 as the information of the imaging state. The information is not necessarily character information and an icon or an image corresponding to the character information may be displayed in place of the character information.

In this manner, for example, even if the inspector is not used to the operation, the inspector can easily notice that the image has a quality problem. If the image index value exceeds the threshold value, a message such as "good image quality" may be displayed. Then, the user can understand that the image has no quality problems.

Further, if the value of the peak_ratio is low and the value of the Imax is high as described above, the output unit 150 causes the display unit 160 to display a message indicating that the ophthalmologic imaging apparatus needs correction of aberration. According to this message, the user can understand that the correction of aberration is necessary.

Further, if the value of the peak_ratio is high and the value of the Imax is low, a message indicating that an increase in imaging light quantity is necessary is displayed on the display unit 160. In this manner, the user can understand that a light quantity adjustment is necessary.

Further, as information other than the information of the imaging state, the density information of the photoreceptor cells may be displayed based on the position of the rmax. Further, a character or a graphic that notifies the user that a blood vessel or a lesion region is extracted instead of the photoreceptor cells on the planar image of the fundus of the eye may be displayed.

The output unit 150 also causes the display unit 160 to display a frequency image, such as the one illustrated in FIG. 4, together with the image of the fundus of the eye. Further, a graph, such as the one illustrated in FIG. 7, may also be displayed. In this manner, detailed information of the imaging state can be presented to the user. Additionally, information of a distribution state of the photoreceptor cells such as density information may be displayed on the display unit. This information is based on the diameter of the ring structure extracted by the feature extraction unit 142. Further, a message informing the user that the image includes a region not including photoreceptor cells (i.e., a blood vessel or a lesion portion) can be displayed on the display unit.

Feature quantity and other information stored in the storage unit 130 in steps S210 to S250 are stored in a database.

According to the above-described configuration, an index useful in objectively evaluating the image quality of a planar image of a fundus of the eye captured by the adaptive optics SLO apparatus can be presented. According to the presentation of such an index, for example, when a diagnosis or a determination of an effect of a treatment is performed using the density of the photoreceptor cells, an objective criterion for determination can be presented.

According to the first exemplary embodiment, a Fourier image is obtained by a frequency conversion of the entire planar image of the fundus of the eye obtained by the adaptive optics SLO, and an index useful for evaluating the image quality of the entire planar image of the fundus of the eye is calculated by extracting various feature quantities from the obtained Fourier image. However, since the image quality of the planar image of the fundus of the eye is not always consistent and the lesion portions may be unevenly distributed in one planar image, the intensity of the periodicity structure of the photoreceptor cells may be different depending on the portion.

According to a second exemplary embodiment, in order to obtain such a local difference, the planar image of the fundus of the eye is segmented into a plurality of local regions. Then, a Fourier image is acquired for each of the planar images of the fundus of the eye acquired by the segmentation, and the planar image is analyzed using the feature quantities extracted from the Fourier images.

Figure 11:
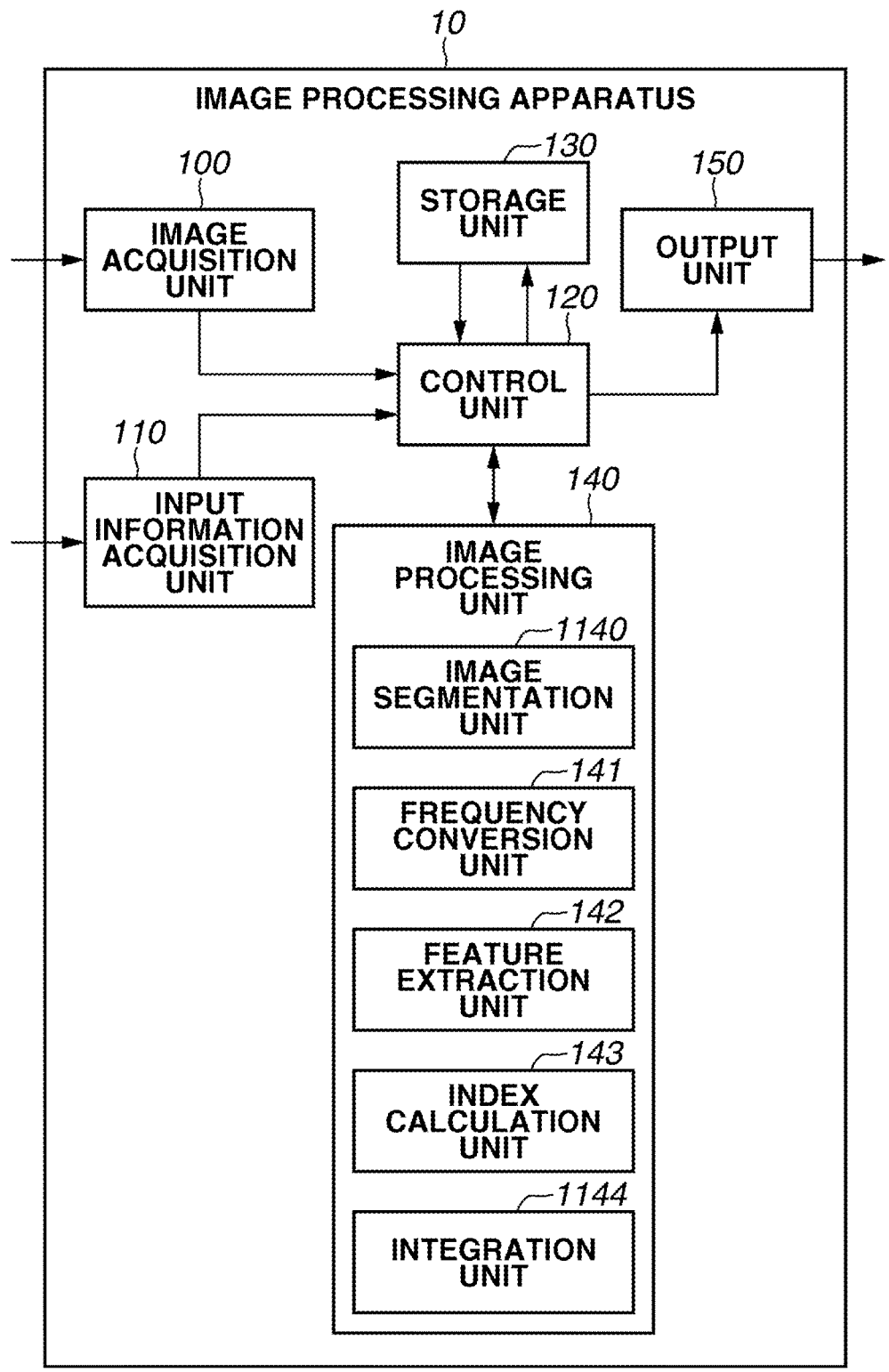
FIG. 11 is a functional configuration of the image processing apparatus according to a second exemplary embodiment.

FIG. 11 illustrates a functional configuration of the image processing apparatus 10 according to the present embodiment. Since the functional configurations of units other than the image processing unit 140 are similar to those illustrated in FIG. 1, their descriptions are not repeated. According to the present embodiment, the image processing unit 140 further includes an image segmentation unit 1140 and an integration unit 1144 as well as the frequency conversion unit 141, the feature extraction unit 142, and the index calculation unit 143. After the planar image of the fundus of the eye is segmented into a plurality of regions, a feature quantity of each region is extracted. The acquired feature quantities are integrated into an integrated index. Then, the image is evaluated according to the integrated index.

The image segmentation unit 1140 segments the planar image of the fundus of the eye into a plurality of partial regions. The frequency conversion unit 141 performs the frequency conversion for each partial region and obtains a partial frequency image. The feature extraction unit 142 extracts a feature quantity based on the ring structure that appears on the partial frequency image. The index calculation unit 143 acquires the information of the photoreceptor cells in the plurality of partial regions.

By obtaining the frequency image for each partial region, if a region where the photoreceptor cells are not extracted is included in the original image, the image can be segmented into a partial region where, for example, a blood vessel is extracted but photoreceptor cells are not extracted, and a partial region other than such a region. Extremely fine blood vessels and lesion portions buried in the noise and unable to determine from the feature quantity of the frequency image are not considered in the segmentation.

Figure 12:
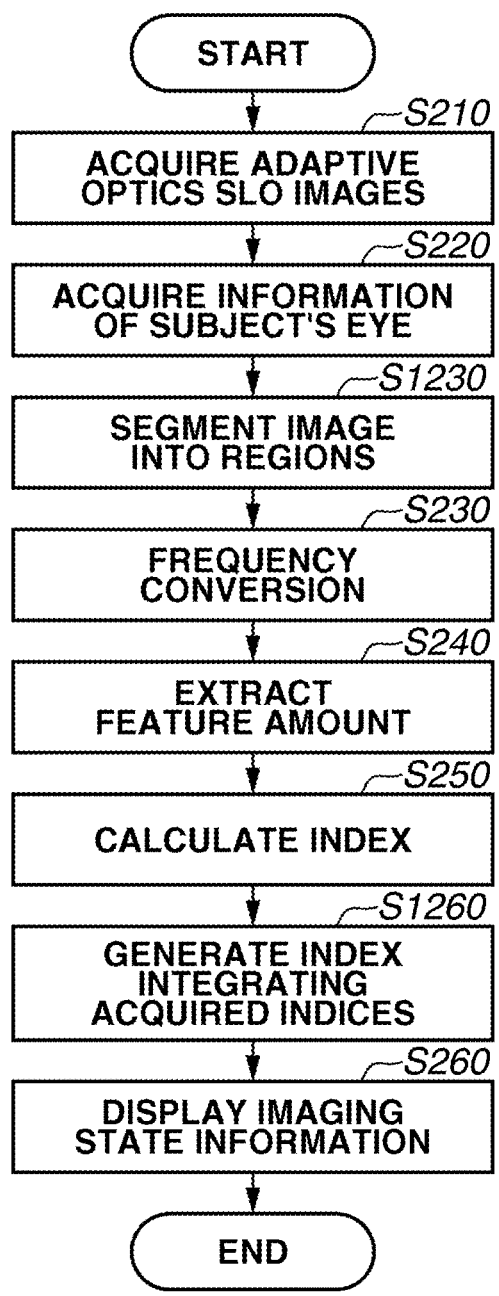
FIG. 12 is a flowchart illustrating processing procedures of the image processing apparatus according to the second exemplary embodiment.

Processing procedures of the image processing apparatus 10 according to the present embodiment is described with reference to the flowchart of FIG. 12. Since the processing procedures insteps S210, S220, S230, S240, and S250 are similar to the processing procedures described according to the first exemplary embodiment, their descriptions are not repeated.

According to the first exemplary embodiment, the calculation of the image quality index is performed with respect to the entire planar image of the fundus of the eye acquired by the adaptive optics SLO. According to the present embodiment, the planar image of the fundus of the eye is segmented into a plurality of local regions, and the index of each region is calculated. Then, the indices are combined and used for the evaluation of the entire image. Thus, the image processed in steps S230, S240, and S250 is a local planar image of the fundus of the eye obtained by the segmentation of the planar image of the fundus of the eye.

Next, each step will be described in detail.

Figure 13:
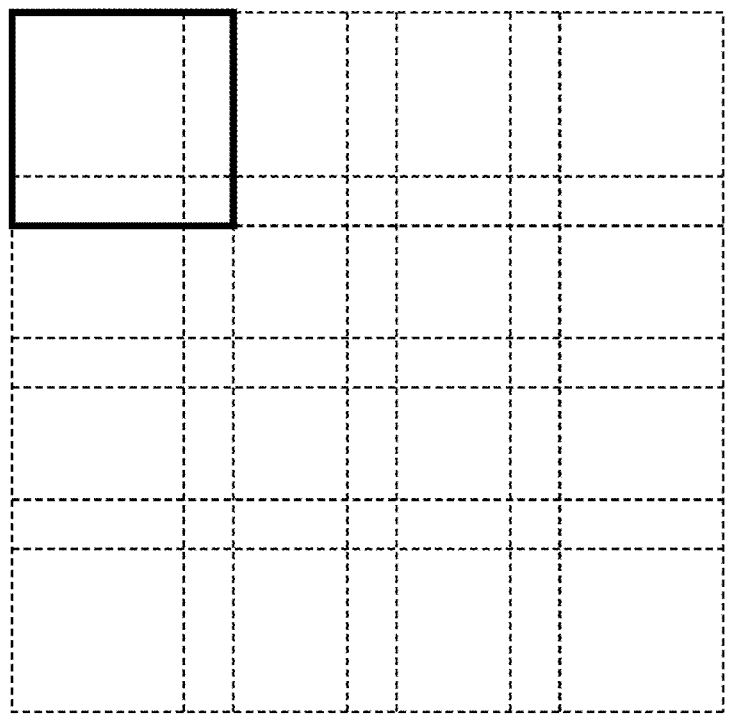
FIG. 13 illustrates an example of dividing the planar image of the fundus of the eye into a plurality of local planar images of the fundus of the eye.

In step S1230, the image segmentation unit 1140 segments the planar image of the fundus of the eye acquired by the adaptive optics SLO and stored in the storage unit 130 into a plurality of local regions. Various methods can be used for the segmentation. Although the local difference can be more noticeable if the planar image of the fundus of the eye is segmented into a great number of small regions, the accuracy of the information obtained from each local region will be reduced. Further, since the frequency conversion of a plurality of regions requires more time and cost, it is important to use an image size of data of 2 to the n-th power suitable for high speed Fourier transform. In the present embodiment, for example, with respect to the original planar image of the fundus of the eye having a size of 400×400, a plurality of local planar images of the fundus of the eye with a size of 128×128 are acquired as described in FIG. 13. Each of the local planar images includes an overlapping portion. The segmentation method, however, is not limited to such an example.

Sixteen local planar images of the fundus of the eye generated in this manner are stored in the storage unit 130 via the control unit 120. Although the processing in steps S230, S240, and S250 is similar to the processing in the first exemplary embodiment, it is different in that the processing is performed for each of sixteen local planar images of the fundus of the eye generated in step 1230. Accordingly, sixteen indices are obtained. Further, each of the obtained indices and the feature quantities acquired in the course of process is stored in the storage unit 130 in association with the corresponding local planar image of the fundus of the eye.

In step S1260, the integration unit 1144 generates an index by integrating the indices acquired from each local planar image of the fundus of the eye. Then, the obtained index is displayed on the monitor via the output unit 150. Further, the feature quantity and other information stored in the storage unit 130 in steps S210 to S1260 are stored in the database.

Figure 14A:
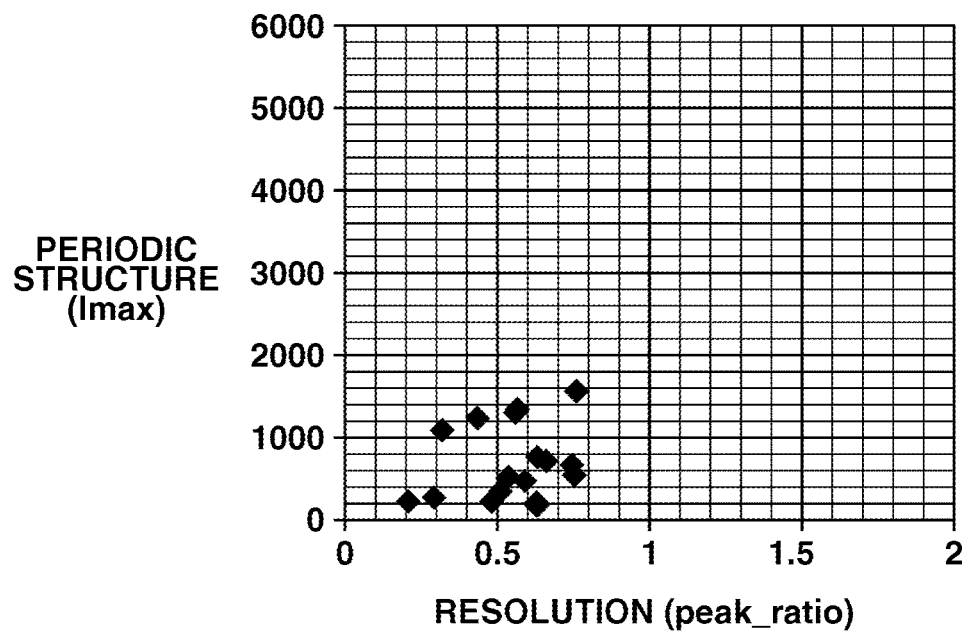
FIGS. 14A and 14B illustrate examples of indices acquired from the local planar images of the fundus of the eye.
Figure 14B:
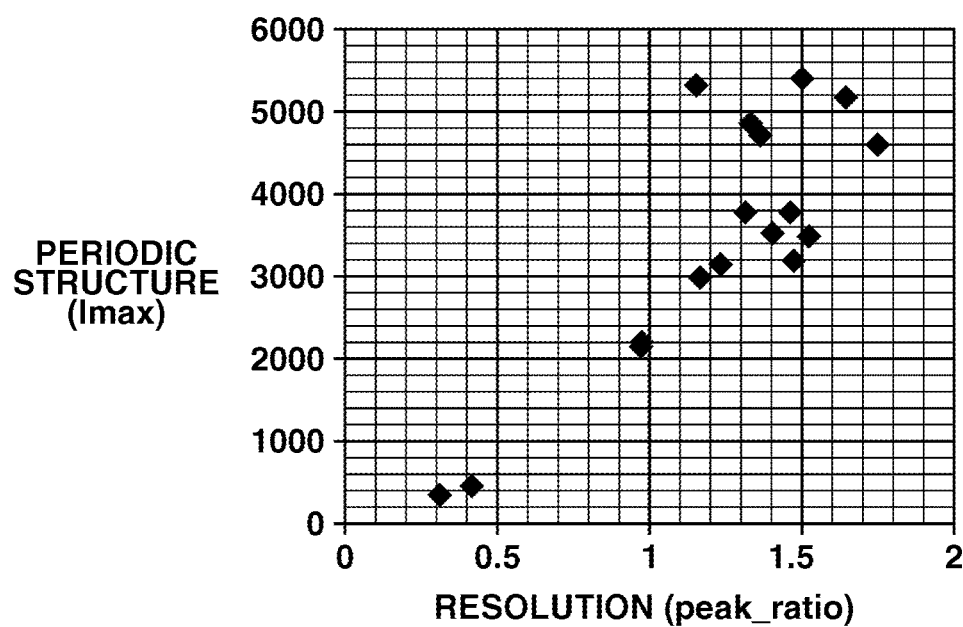

FIGS. 14A and 14B illustrate examples of sixteen indices acquired in step S250. In FIG. 14A, all of the sixteen indices show poor image quality. If the state of the subject's eye is not good and, for example, the crystalline lens is very cloudy, very few signals can be obtained. In such a case, all the indices acquired from the local planar images of the fundus of the eye show bad values. Thus, if indices such as those illustrated in FIG. 14A are obtained, the quality of the planar image of the fundus of the eye is considered as low as a whole.

On the other hand, if the indices of both high values and of low values are determined as illustrated in FIG. 14B, it can be considered that some of the local regions failed in the acquisition of the periodic structure of the photoreceptor cells although the imaging itself has been successful. Such a case indicates that the photoreceptor cells are not extracted due to, for example, the existence of a blood vessel, or the photoreceptor cells do not exist due to, for example, a lesion.

Regarding the extraction of a blood vessel from a planar image of a fundus of the eye acquired by an adaptive optics SLO, there is a known method such as the one discussed in Tam, J., Martin, J. A., Roorda, A., "Non-invasive visualization and analysis of parafoveal capillaries in humans" Invest. Ophthalmol. Vis. Sci. 51 (3): 1691-1698 (2010). If indices such as those illustrated in FIG. 14B are obtained according to a combination of such methods, whether the possibility of the local region, indicating the low index value, having a blood vessel or a lesion portion is high can be determined.

Further, the planar image can be evaluated by a combination of the first and the second exemplary embodiments, for example, a combination of the overall evaluation and the partial evaluation. By presenting a result obtained from the combined evaluation, even if the overall evaluation is not good, the evaluation will be useful since the user can determine the reason for the poor evaluation (e.g., poor imaging condition, lesion portion was included). This is useful as if any part of the partial evaluation indicates high image quality, the possibility of the imaging condition being the cause of the poor image quality is low. Thus, an optimum index can be presented by combining the evaluation methods.

According to the present embodiment, the planar image of the fundus of the eye acquired by the adaptive optics SLO apparatus is segmented into a plurality of local regions. Further, the image quality indices obtained from the local planar images of the fundus of the eye are integrated to form an integrated index. According to this index, a case where the overall image quality of the fundus of the eye is low and a case where the image quality itself is not low but a region where the periodic structure of the photoreceptor cells is not extracted exists due to the presence of a blood vessel or a lesion region can be presented.

Further, the ophthalmologic imaging apparatus can be configured such, from the aspect of hardware, that the index calculation unit 143 automatically determines a lesion region. Then, based on the result of the determination, the output unit 150 outputs information regarding the imaging region to the apparatus. On receiving the information, the apparatus automatically captures the image again by setting the center of the image to that imaging region.

If the output unit 150 outputs an aberration correction instruction or a control value of an adjustment value of a light quantity according to the imaging state to the ophthalmologic imaging apparatus, then the ophthalmologic imaging apparatus controls the aberration measurement unit and the correction optical system based on the input control value. Accordingly, the user does not need to adjust the apparatus.

According to the first exemplary embodiment, the information of the imaging state is displayed and the user performs the operation according to the displayed information. According to a third exemplary embodiment, the information of the imaging state is used for forming and selecting an image. Since the configurations of the apparatus are similar to those described in the first and the second exemplary embodiments, their descriptions are not repeated and the points different from the above-described exemplary embodiments will be mainly described.

The image acquisition unit 100 acquires a plurality of planar images of the fundus of the eye obtained by imaging of different or substantially same positions. Since the fundus of the eye moves due to the involuntary eye movement such as a saccade, even if a tracking function is provided, the tracking may not be successful. Thus, even if the apparatus is set to capture an image of the same position, actually, an image of a different position may be captured. This is why the expression "substantially the same" is used.

The image processing unit 140 functions as a determination unit configured to determine the image quality. The image processing unit 140 acquires the information of the imaging state acquired by the index calculation unit 143 and the information of the threshold value of the imaging state determined in advance. Then, the image processing unit 140 determines whether the imaging state obtained for each image exceeds or falls below the threshold value. As the information of the imaging state, for example, the values of the peak_ratio and Imax described in the first exemplary embodiment or an image quality index value obtained by a combination of such values can be used.

Additionally, the image processing unit 140 functions as a selection unit configured to select an image. If an image is determined by the determination unit as having an image quality below the threshold value, the image processing unit 140 determines that it is inappropriate for the presentation to the user or not suitable for the superimposing processing and does not select the image. In other words, the image processing unit 140 selects only the images that exceed the threshold value. Since the images below the threshold value are not selected, images with aberration, images with insufficient light quantity, and images captured when the eye instantaneously moved due to blinking or the like are not selected by the image processing unit 140.

The image processing unit 140 further aligns the selected images and performs the superimposing processing. Thus, the image processing unit 140 also functions as a generation unit configured to generate an image with reduced random noise. Accordingly, the image quality of a plurality of images can be automatically determined and a planar image of a fundus of the eye with good image quality can be obtained.

The control unit 120 outputs only the image selected from the acquired plurality of images to the output unit 150. The control unit 120 outputs such an image together with the generation unit or in place of the generation unit. The output unit 150 causes the display unit 160 to display only the selected image. The unselected images are not transmitted to the output unit 150 but is stored in the storage unit 130.

The unselected images can be deleted as a failed image with the approval of the user. In addition to the display of the image for the diagnosis, the output unit 150 can separately display the images which have not been selected on the display unit 160 and further display a window that accepts the approval of the user regarding the deletion. The control unit 120 can delete the approved images from the storage unit 130 in one operation. Further, in place of the deletion, the control unit 120 can cause only the approved images not to be transferred to the external database. In this manner, the user can automatically determine unnecessary images and can easily perform the deletion processing or the non-transfer processing.

Figure 15:
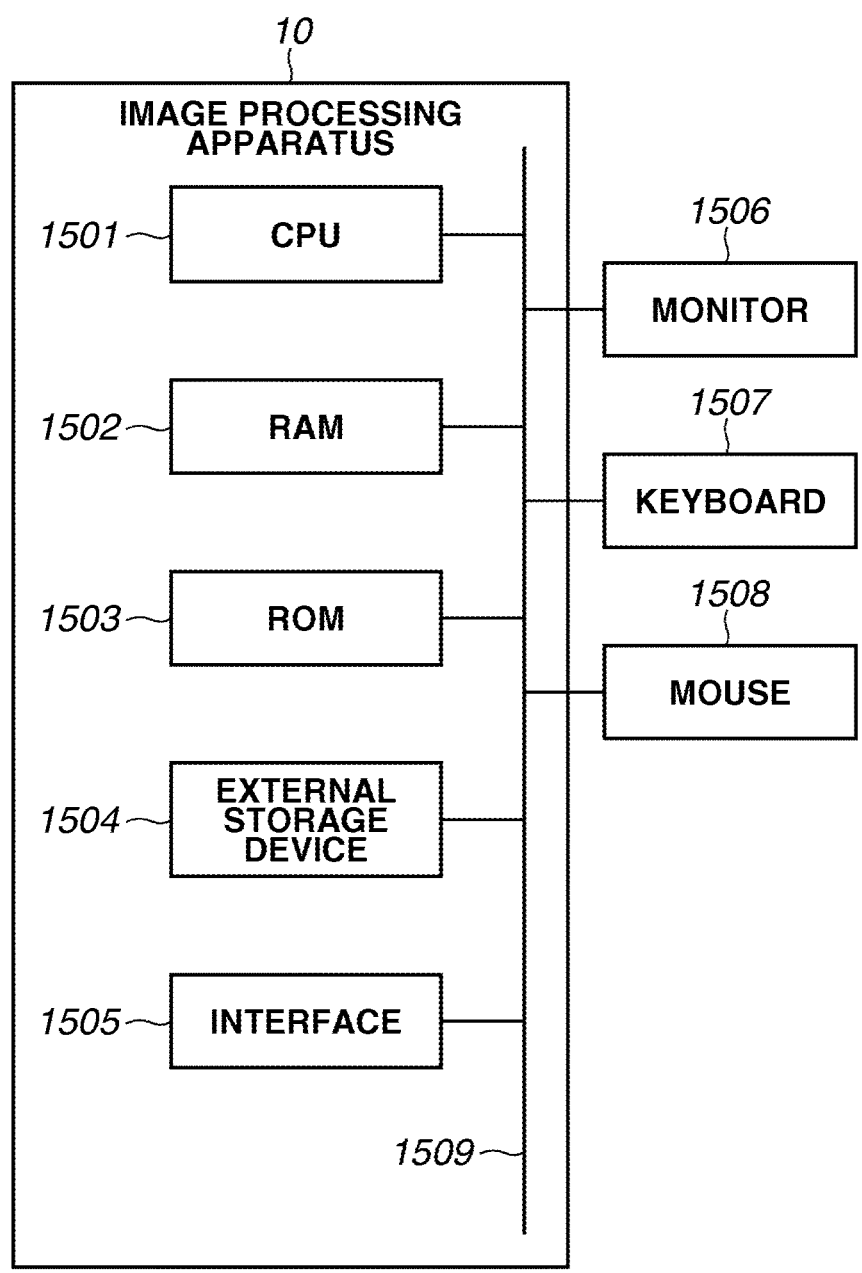
FIG. 15 illustrates a hardware configuration of the image processing apparatus according to another exemplary embodiment.

The function of the above-described image processing apparatus 10 can be realized by the hardware illustrated in FIG. 15 and using the software and hardware together.

The image processing apparatus illustrated in FIG. 15 includes a central processing unit (CPU) 1501, a random access memory (RAM) 1502, a read only memory (ROM) 1503, an external storage unit 1504, and a communication interface 1505. These units are connected to each other via a bus 1509. Further, a monitor 1506, a keyboard 1507, and a mouse 1508 are connected to the image processing apparatus 10. A program including an instruction that can cause the processing illustrated in the flowchart of FIG. 2 or 12 is stored in the ROM 1503 or the external storage unit 1504.

The function of the image processing apparatus 10 of the above-described exemplary embodiment is realized by the CPU 1501 reading out a stored program, loading it into the RAM 1502, and executing the instruction included in the program.

Figure 16:
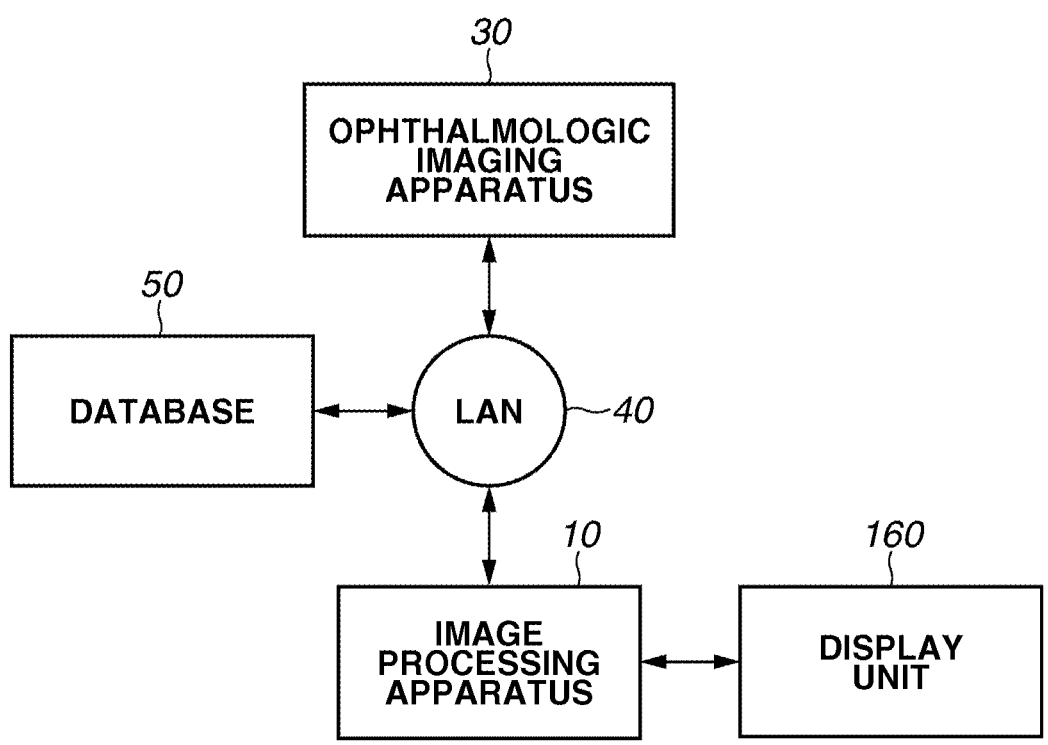
FIG. 16 illustrates a configuration of an ophthalmologic imaging system.

An example of an imaging system which acquires a planar image of the fundus of the eye described above will be described with reference to FIG. 16. The image processing apparatus 10 in the imaging system is connected to an ophthalmologic imaging apparatus 30 and a database 50 via a local area network (LAN) 40. The image processing apparatus 10 can be wirelessly connected to the LAN 40. Further, the display unit 160 is connected to the image processing apparatus 10.

The configuration of the imaging system is not limited to the above-described example. For example, an ophthalmologic imaging apparatus which includes an ophthalmologic imaging unit, an image processing unit, and the display unit 160 may be used. In this case, the ophthalmologic imaging unit includes the function of the ophthalmologic imaging apparatus 30 and the image processing unit includes the function of the image processing apparatus 10. If the imaging system has such a configuration, the quality of the image of the photoreceptor cells can be determined by the ophthalmologic imaging apparatus 30 alone, and the system can be downsized.

Configuration of the ophthalmologic imaging apparatus 30 will be described with reference to FIG. 17.

A composite apparatus composed of an SLO apparatus and an OCT apparatus according to the embodiments of the present invention is described as an ophthalmologic imaging apparatus. In particular, the ophthalmologic imaging apparatus 30 which includes an adaptive optical system and can capture both planar images (SLO images) of high lateral resolution as well as tomographic images (OCT images) for a retina and acquires a planar image of a fundus of the eye will be described. The ophthalmologic imaging apparatus 30 includes an SLO apparatus and an OCT apparatus. The SLO apparatus acquires a planar image of a fundus of the eye by correcting the optical aberration of the subject's eye and using a spatial light modulator. The OCT apparatus employs Fourier domain imaging when it acquires a tomographic image. According to these apparatuses, the ophthalmologic imaging apparatus 30 can obtain a good planar image of the fundus of the eye and a tomographic image of the subject's eye regardless of the visibility and the optical aberration.

First, an overall configuration of the ophthalmologic imaging apparatus 30 according to the present embodiment will be described in detail with reference to FIG. 17. Light emitted from a light source 201 is divided into a reference beam 205 and a measuring beam 206 by an optical coupler 231. The measuring beam 206 is guided to a subject's eye 207 as an object to be observed via a single mode fiber 230-4, a spatial light modulator 259, an XY scanner 219, an X scanner 221, and spherical mirrors 260-1 to 260-9.

The measuring beam 206 is reflected or scattered by the subject's eye 207 being an object to be observed and returned as a return beam 208. The return beam 208 enters a detector 238 or a line sensor 239. The detector 238 converts the light intensity of the return beams 208 into a voltage signal. Then, based on the voltage signal, a planar image of the fundus of the eye of the subject's eye 207 is generated. Further, the return beam 208 is combined with the reference beam 205, and the combined light is caused to enter the line sensor 239. Accordingly, a tomographic image of the subject's eye 207 is formed. Furthermore, by using a plurality of acquired tomographic images, a three-dimensional course of blood vessels can be extracted.

Although a spatial light modulator is used as a device for correcting the wavefront aberration, in the present embodiment, any device can be used so long as the wavefront aberration can be corrected. Thus, for example, a variable shape mirror can be used.

Next, the periphery of the light source 201 will be described. The light source 201 uses a super luminescent diode (SLD) being a typical low-coherent light source. The central wavelength and the bandwidth are 830 nm and 50 nm, respectively. In order to acquire a planar image of the fundus of the eye with small speckle noise, a low-coherent light source is selected. Although the SLD is selected as a type of the light source, a different light source can be used so long as low coherent light can be emitted. For example, an amplified spontaneous emission (ASE) light source can be used.

Further, near-infrared light is suitable as a wavelength from the viewpoint of measurement of eyes. Further, since the wavelength affects the lateral resolution of the acquired planar image of the fundus of the eye, a shorter wavelength is desirable. In the descriptions below, a wavelength of 830 nm is used. Other wavelengths may be selected depending on the measuring portion of the object to be observed.

Light emitted from the light source 201 is divided into the reference beam 205 and the measuring beam 206 at a ratio of 96:4 via a single mode fiber 230-1 and the optical coupler 231. The composite apparatus 30 further includes polarization controllers 253-1 and 253-2.

Next, an optical path of the reference beam 205 will be described.

The reference beam 205 divided by the optical coupler 231 is adjusted so that it is guided to a lens 235-1 via a single mode fiber 230-2 and adjusted so as to become parallel light with a beam diameter of 4 mm.

Next, the reference beam 205 is guided to a mirror 214 being a reference mirror by mirrors 257-1 to 257-4. Since the optical path length of the reference beam 205 is adjusted to be substantially the same as that of the measuring beam 206, the reference beam 205 and the measuring beam 206 interfere with each other. Next, the reference beam 205 is reflected by the mirror 214 and guided again to the optical coupler 231. A dispersion compensation glass 215, through which the reference beam 205 passes, compensates the dispersion that occurs when the measuring beam 206 travels to the subject's eye 207 and returns from the subject's eye 207 with respect to the reference beam 205. In the following descriptions, for example, an average diameter of an oculus of a Japanese being L1=23 mm is used.

A motorized stage 217-1 is movable in the directions indicated by an arrow to allow the optical path length of the reference beam 205 to be adjusted and controlled. Further, the motorized stage 217-1 is driven by a motorized stage driver 283 in a driver unit 281 under the control of a personal computer 225.

Next, the optical path of the measuring beam 206 will be described. The measuring beam 206 split by the optical coupler 231 is guided to a lens 235-4 via the single mode fiber 230-4 and adjusted so as to become parallel light with a beam diameter of 4 mm. Further, the polarization controller 253-1 or 253-2 can adjust the polarization state of the measuring beam 206. In the present embodiment, the polarization controller 253-1 or 253-2 adjusts the polarization state of the measuring beam 206 to be linearly polarized in a direction parallel to the drawing surface of FIG. 17.

The measuring beam 206 passes through a beam splitter 258 and a movable beam splitter 261 (also referred to as a splitting unit) and reaches the spatial light modulator 259 via the spherical mirrors 260-1 and 260-2. Then, the measuring beam 206 is modulated at the spatial light modulator 259. In the present embodiment, the spatial light modulator 259 utilizes the orientation characteristics of the liquid crystal. More specifically, the spatial optical modulator 259 is arranged in a direction where the spatial optical modulator 259 can modulate the phase of linear polarization parallel to the drawing surface of FIG. 17 (i.e., the P polarization) to coincide with the polarization orientation of the measuring beam 206.

Further, the measuring beam 206 passes through a polarizing plate 273 and reaches a mirror of the X scanner 221 via the spherical mirrors 260-3 and 260-4. In the present embodiment, the polarizing plate 273 has a role to guide only the linear polarization parallel to the drawing surface of FIG. 17, of the return beams 208, to the spatial light modulator 259. Further, in the present embodiment, the X scanner 221 scans the measuring beam 206 in a direction parallel to the drawing surface of FIG. 17. For example, the X scanner 221 is a resonant scanner having a drive frequency of approximately 7.9 kHz.

Further, the measuring beam 206 is incident on a mirror of the XY scanner 219 via the spherical mirrors 260-5 and 260-6. Although the number of the mirrors in the XY scanner 219 is illustrated as one, actually, the XY scanner 219 includes two mirrors (X-scanning mirror and Y-scanning mirror) arranged close to each other. Further, the measuring beam 206 is adjusted in such a manner that its center coincides with the center of rotation of the mirror of the XY scanner 219. The drive frequency of the XY scanner 219 is changeable in the range up to 500 Hz.

The spherical mirrors 260-7 to 260-9 are optical systems that cause the measuring beam 203 to scan a retina 227. Having a point near a cornea 226 as a support point, the measuring beam 206 scans the retina 227. Although the measuring beam 206 has a beam diameter of 4 mm, the beam diameter may be increased for acquisition of a high resolution tomographic image.

Figure 17:
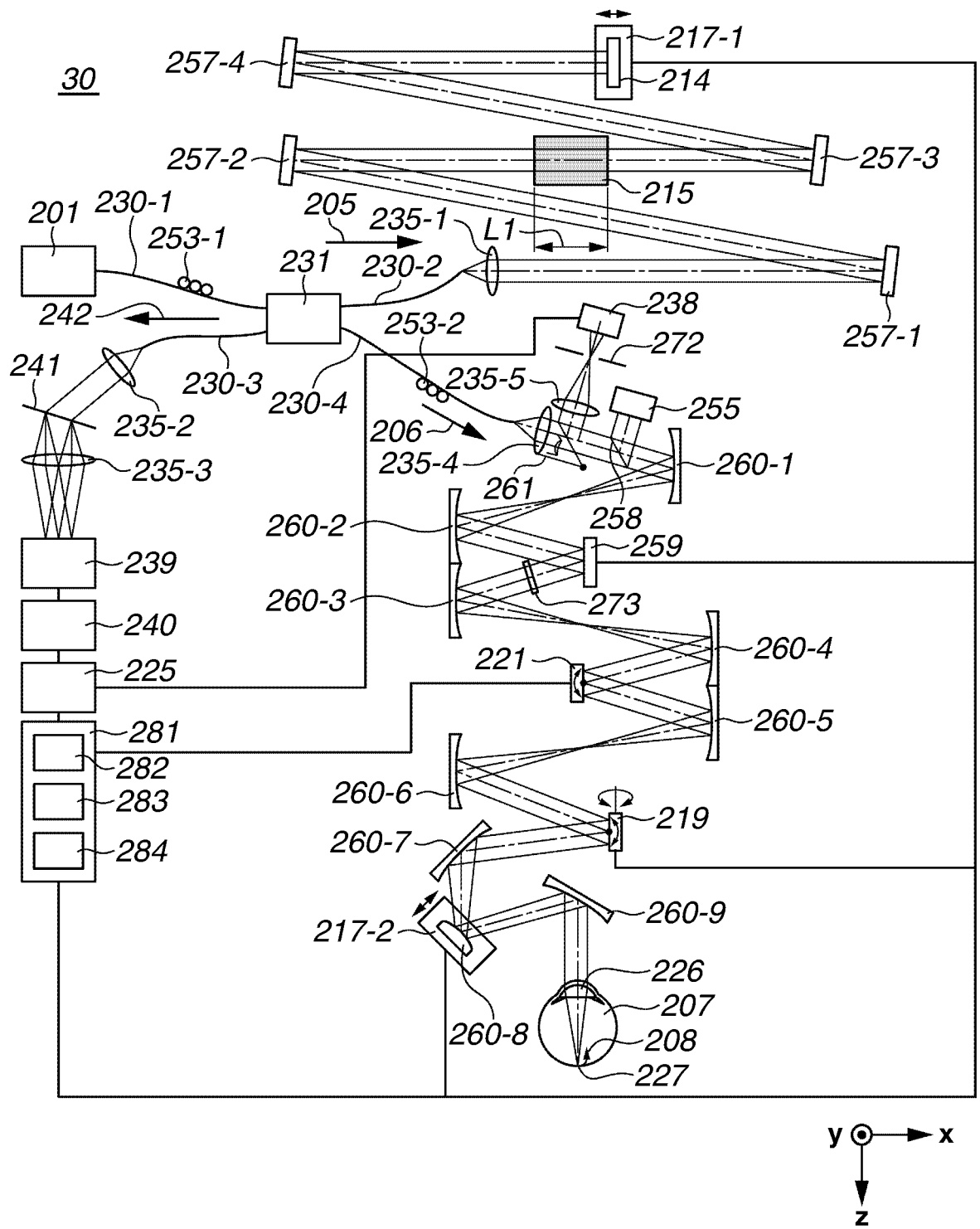
FIG. 17 illustrates a configuration of an ophthalmologic imaging apparatus.

A motorized stage 217-2 is configured to move in a direction indicated by an arrow in FIG. 17 and to adjust and control the position of a spherical mirror 260-8 attached thereto. Similarly to the motorized stage 217-1, the motorized stage 217-2 is controlled by the motorized stage driver 283.

By adjusting the position of the spherical mirror 260-8, it is possible to focus the measuring beam 206 on a predetermined layer of the retina 227 of the subject's eye 207 and observe the subject's eye 207. In the initial state, the position of the spherical mirror 260-8 is adjusted so that the measuring beam 206 can enter the cornea 226 as parallel light. The ophthalmologic imaging apparatus 30 according to the present embodiment can cope with the subject's eye 207 having a refractive error.

When the measuring beam 206 enters the subject's eye 207, the measuring beam 206 becomes the return beam 208 due to reflection or scattering from the retina 227. Then, the return beam 208 reaches the line sensor 239 by being guided again by the optical coupler 231. A part of the return beam 208 is reflected by the movable beam splitter 261 and guided to the detector 238 via a lens 235-5.

A light blocking plate 272 having a pinhole has a function of blocking unnecessary light not focused on the retina 227 among the return beams 208. Further, the light blocking plate 272 is arranged in a position conjugate with the focusing position of the lens 235-5. The diameter of the pinhole of the light blocking plate 272 is, for example, 50 μm. As the detector 238, for example, an avalanche photodiode (APD), which is a high-speed, highly-sensitive light sensor, is used. Apart of the return beam 208 split by the beam splitter 258 enters a wavefront sensor 255. The wavefront sensor 255 is a Shack-Hartmann wavefront sensor.

The spherical mirrors 260-1 to 260-9 are arranged so that they are optically conjugate with the XY scanner 219, the X scanner 221, the cornea 226, the wavefront sensor 255, and the spatial light modulator 259. Thus, the wavefront sensor 255 can measure the aberration of the subject's eye 207. Further, the spatial light modulator 259 can correct the aberration of the subject's eye 207. Furthermore, by controlling the spatial light modulator 259 in real time based on the obtained aberration, it is possible to correct the aberration that occurs in the subject's eye 207 and to acquire tomographic images with higher lateral resolution.

Next, the configuration of the measurement system will be described. The ophthalmologic imaging apparatus 30 can acquire tomographic images (OCT images) as well as planar images of the fundus of the eye (SLO images).

First, the measurement system for the tomographic images will be described. The return beams 208 are combined by the optical coupler 231. The combined light (combined light 242) is guided to a transmissive grating 241 via a single mode fiber 230-3 and a lens 235-2, and is dispersed for each wavelength. Then, the light enters the line sensor 239 via a lens 235-3.

The line sensor 239 converts the light intensity for each position (wavelength) into a voltage signal. The voltage signal is converted into a digital value by a frame grabber 240 so that tomographic images of the subject's eye 207 are formed in the personal computer 225. The line sensor 239 includes 1024 pixels and can obtain the intensity of the combined light 242 for each wavelength (a segmentation of 1024).

Next, the measurement system for the planar image of the fundus of the eye will be described. A part of the return beam 208 is reflected by the movable beam splitter 261. After unnecessary light is blocked by the light blocking plate 272, the reflected light reaches the detector 238, and the light intensity is converted into an electric signal. Data of the obtained electric signal is processed by the personal computer 225 in synchronization with the scanning signal of the X scanner 221 and the XY scanner 219. Accordingly, a planar image of the fundus of the eye is formed.

Apart of the return beam 208 split by the beam splitter 258 enters the wavefront sensor 255, and the aberration of the return beam 208 is measured. An image signal obtained by the wavefront sensor 255 is supplied to the personal computer 225, and the aberration is calculated. The obtained aberration is expressed by Zernike polynomial, which represents the aberration of the subject's eye 207. The Zernike polynomial includes a tilt term, a defocus term, an astigmatism term, a coma term, and a trefoil term.

Next, an acquisition method for tomographic images (OCT images) using the ophthalmologic imaging apparatus 30 will be described with reference to FIGS. 18A to 18C. The ophthalmologic imaging apparatus 30 acquires a tomographic image of the retina 227 by controlling the XY scanner 219 and acquiring an interference fringe by the line sensor 239 using the X scanner 221 as a fixed mirror. The movable beam splitter 261 is controlled so that the return beams 208 are not guided to the detector 238. Further, the X scanner 221 and the XY scanner 219 are controlled by an optical scanner driver 282 in the driver unit 281 from the personal computer 225. In the present embodiment, the method for acquiring a tomographic image (a plane parallel to the optical axis) of the retina 227 will be described.

Figure 18A:
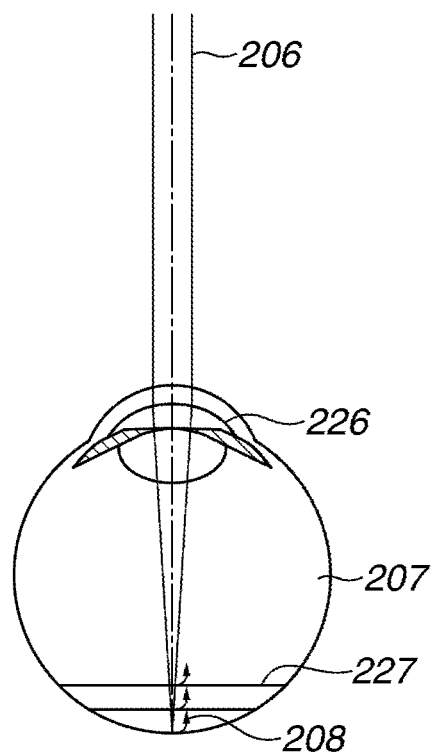
FIGS. 18A, 18B, and 18C illustrate an image acquisition method for optical coherence tomography (OCT).
Figure 18B:
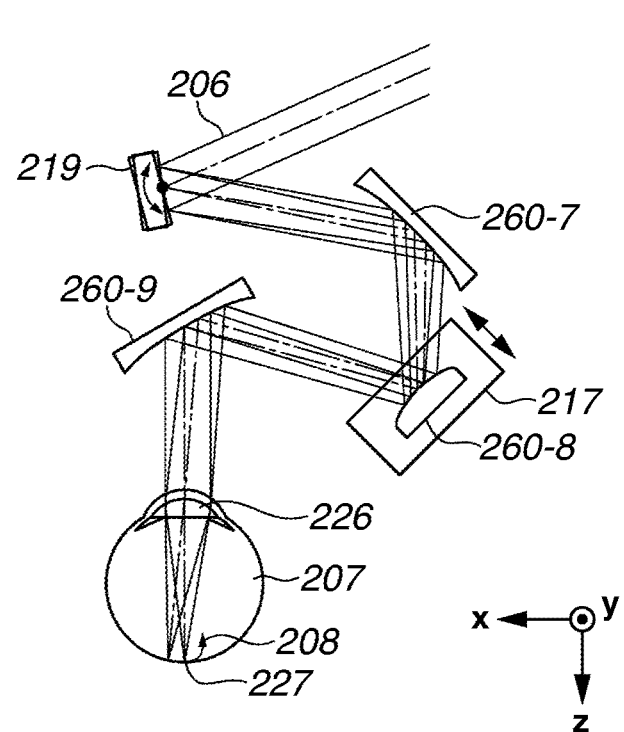

FIG. 18A is a schematic view of the subject's eye 207 and illustrates a state where the subject's eye 207 is observed by the ophthalmologic imaging apparatus 30. As illustrated in FIG. 10A, when the measuring beam 206 enters the retina 227 via the cornea 226, the measuring beam 206 becomes the return beams 208 due to reflection or scattering at various positions. Then, the return beam 208 reaches the line sensor 239 with delays at the respective positions.

Since the light source 201 has a large bandwidth and a short coherence length, the line sensor 239 can detect an interference fringe when the optical path length of the reference beam path is approximately equal to the optical path length of the measuring beam path. As described above, the interference fringe acquired by the line sensor 239 is an interference fringe in a spectrum region on the wavelength axis.

Subsequently, the interference fringe, which is information of the wavelength axis, is converted into an interference fringe on an optical frequency axis considering the characteristics of the line sensor 239 and the transmissive grating 241. Further, by performing inverse Fourier transform of the obtained interference fringe on the optical frequency axis, it is possible to obtain information in the depth direction. As illustrated in FIG. 18B, if the interference fringe is detected while the XY scanner 219 is driven, the interference fringe can be obtained at each position on the X-axis. More specifically, the information in the depth direction can be obtained at each position on the X-axis. As a result, a two-dimensional distribution of the intensity of the return beams 208 on the XZ plane is obtained, which is a tomographic image 232 (see FIG. 18C).

As described above, the tomographic image 232 is an image obtained by arranging the intensity of each of the return beams 208 in an array. For example, the tomographic image 232 is a gray scale intensity image. The length of the tomographic image 232 in the X direction is 700 µm, which is similar to the SLO image described below.

Figure 18C:
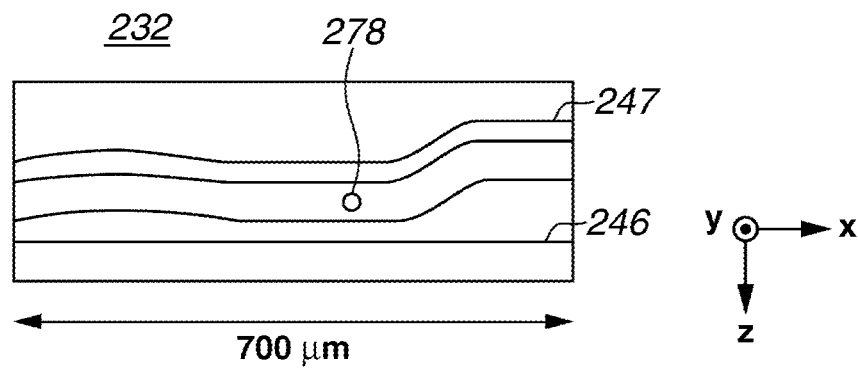

In FIG. 18C, only the boundaries in the obtained tomographic image are expressed in lines. The illustration includes a retinal pigment epithelial layer 246, a stratum opticum 247, and a blood vessel 278. Further, if a plurality of tomographic images is acquired at each position on the Y-axis, it is possible to visualize a three-dimensional course of the blood vessel.

Next, an acquisition method of a planar image of the fundus of the eye (SLO image) using the ophthalmologic imaging apparatus 30 will be described. The ophthalmologic imaging apparatus 30 can acquire a planar image of the fundus of the eye of the retina 227 by controlling and operating the XY scanner 219 in only the Y-axis direction and the X scanner 221 while fixing the X-axis direction of the XY scanner 219, and acquiring the intensity of the return beam 208 using the detector 238.

The X scanner 221 and the XY scanner 219 are controlled by the optical scanner driver 282 in the driver unit 281 from the personal computer 225 (see FIG. 17). Further, the ophthalmologic imaging apparatus 30 can acquire a planar image of the fundus of the eye while correcting the aberration that occurs at the subject's eye 207 by controlling the spatial light modulator 259. The spatial light modulator 259 can be controlled by using the aberration of the subject's eye 207 measured by the wavefront sensor 255. Furthermore, the ophthalmologic imaging apparatus 30 can acquire a planar image of the fundus of the eye while controlling the spatial light modulator 259 in real time.

Next, the acquisition method of the planar image of the fundus of the eye (SLO image) will be described with reference to FIGS. 19A to 19D.

The ophthalmologic imaging apparatus 30 acquires a planar image of a fundus of the eye of the retina 227 by controlling the XY scanner 219 and acquiring the intensity of the return beam 208 by the detector 238. An acquisition method of a planar image of the fundus of the eye of the retina 227 (planar image perpendicular to the optical axis) will now be described.

Figure 19A:
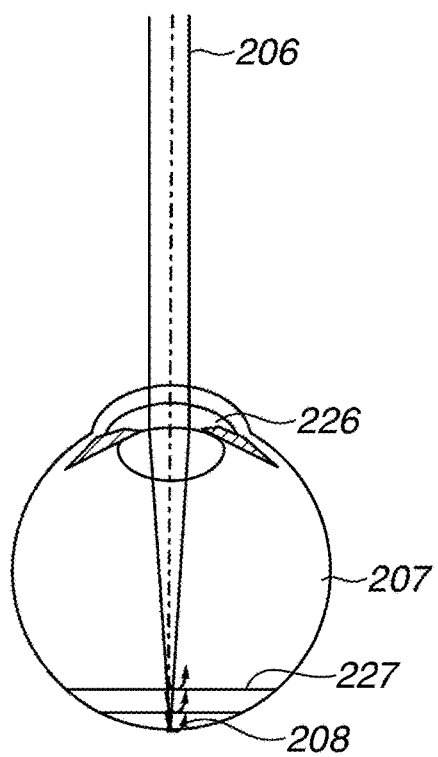
FIGS. 19A, 19B, 19C, and 19D illustrate an image acquisition method for SLO.

FIG. 19A is a schematic view of the subject's eye 207 and illustrates a state where the subject's eye 207 is observed by the ophthalmologic imaging apparatus 30.

Figure 19B:
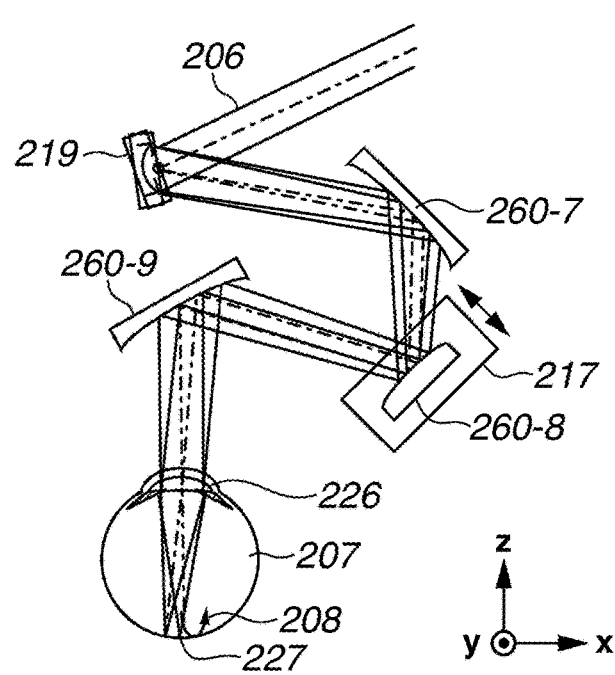

As illustrated in FIG. 19A, when the measuring beam 206 enters the retina 227 via the cornea 226, the measuring beam 206 becomes the return beam 208 due to reflection or scattering at various positions. Then, the return beam 208 reaches the detector 238. Further, as illustrated in FIG. 19B, if the intensity of the return beam 208 is detected while the XY scanner 209 is moved in the X direction, information at each position on the X-axis can be obtained.

Figure 19C:
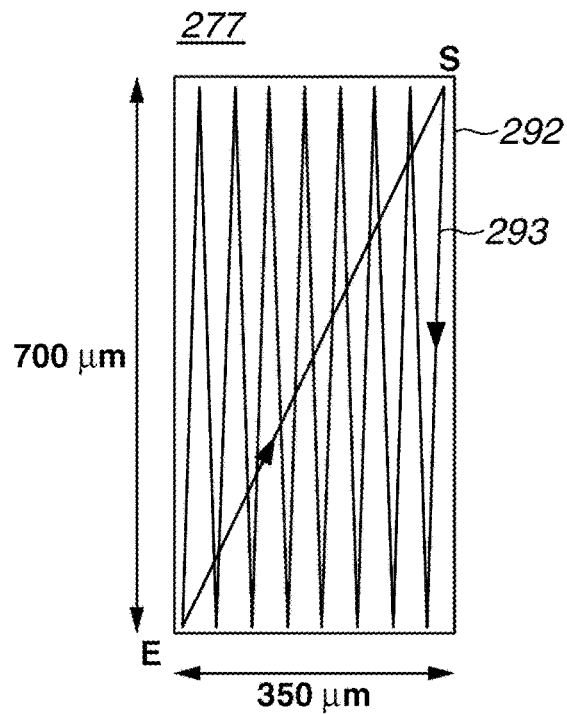

As illustrated in FIG. 19C, the XY scanner 209 is simultaneously moved in both the X-axis and Y-axis directions with respect to an image capturing range 292 where the retina 227 is present. Then, the measuring beam 206 is raster-scanned along a trajectory 293 on the image capturing range 292. In this state, if the intensity of the return beams 208 is detected, a two-dimensional distribution of the intensity of the return beams 208 can be obtained. Accordingly, a planar image of the fundus of the eye 277 (see FIG. 19D) is acquired.

Figure 19D:
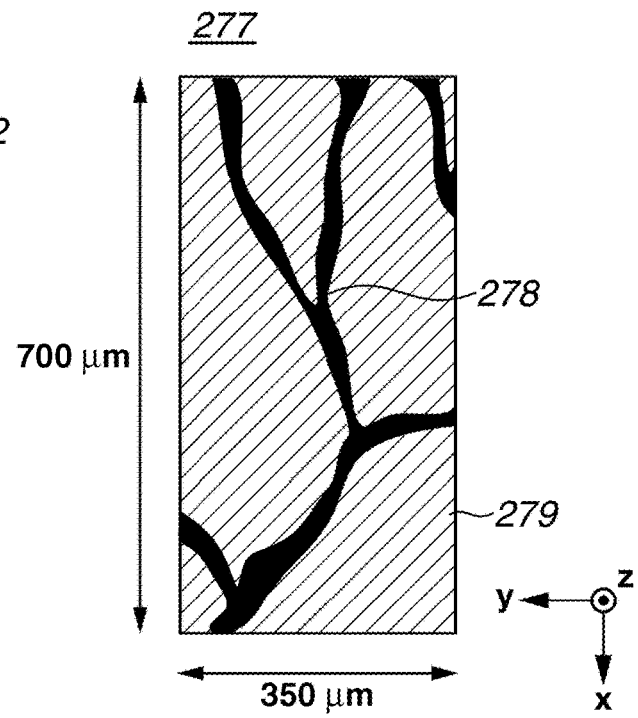

In FIG. 19D, the measuring beam 206 is scanned from a point S at the upper right to a point E at the bottom left. While the scanning is performed, the intensity of the return beams 208 is used in forming the planar image of the fundus of the eye 277. The trajectory 293 from the point E to the point S is the movement of the measuring beam 206 as a preparation for the imaging of the planar image of the fundus of the eye 277 which is to be formed next. The time required for the scanning takes 84% for the point S to the point E and 16% for the point E to the point S with respect to the trajectory 293 in FIG. 19C. This ratio is based on the duty ratio of the drive waveform of the Y scanner described above. Further, in FIG. 19C, for the sake of simplicity, the number of times of the scanning in the X direction with respect to the trajectory 293 is smaller than the actual number of times.

The planar image of the fundus of the eye 277 has a size of 700×350 µm. The time required for the acquisition is approximately 15.6 ms. This time is based on the drive frequency of the Y scanner.

In the planar image 277 of the fundus of the eye, a photoreceptor cell group 279, where the intensity of the return beam 208 is relatively high, is light colored, whereas the blood vessel 278, where the intensity is relatively low, is dark colored. Further, blood cells (not illustrated) are light colored in the blood vessel 278. If the planar image of the fundus of the eye 277 is continuously acquired, the movement of the blood cells through the blood vessel 278 can be visualized. Further, spatio-temporal images may be generated by extracting the blood vessel 278, from which the blood cells are visualized, from the planar images 277 of the fundus of the eye which are continuously acquired, and superimposing the extracted planar images 277 of the fundus of the eye in the order they have been captured. Movement of the blood cells and the blood speed can be easily obtained.

An imaging method for obtaining an image useful for obtaining the blood speed and an imaging method for obtaining an image of the photoreceptor cells are designated by the user via an operation unit of the image processing apparatus 10. When the user selects the imaging method via the operation unit, a designation unit (not illustrated) of the image processing apparatus designates the selected imaging method and transmits associated information to the ophthalmologic imaging apparatus 30. Then, according to the designated imaging method, the ophthalmologic imaging apparatus 30 outputs an image of photoreceptor cells which is easy to observe or an image having a bloodstream as an object to be observed.

The embodiment can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the embodiment of the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An image processing apparatus comprising:
    an obtaining unit configured to obtain a fundus image of an eye;
    a segmentation unit configured to segment the fundus image into a plurality of partial images;
    an identification unit configured to obtain a partial frequency image by performing frequency conversion for each of the plurality of partial images; and
    an information acquisition unit configured to acquire image quality information indicating an image quality of the fundus image based on at least one of the following:
    an intensity value of a peak of a ring structure of the partial frequency image, a sharpness value that indicates a peak status of the ring structure, a position of the peak intensity value in the ring structure, a peak status and a position of a disk structure of the partial frequency image, and a peak intensity value in the disk structure,
    wherein the information acquisition unit further is configured to acquire information about photoreceptor cells in each of the plurality of partial images.

2. The image processing apparatus according to claim 1, wherein, in a case where the information acquisition unit acquires information, the information acquisition unit extracts a blood vessel based on the acquired information.

3. The image processing apparatus according to claim 1, wherein the information acquisition units is configured to extract a blood vessel based on the acquire information being information about the photoreceptor cells in each of the plurality of partial images.

4. The image processing apparatus according to claim 1, wherein the acquired information includes at least one of the following: information of an imaging state of the photoreceptor cells of the fundus image and/or distribution information of the photoreceptor cells of the fundus image.

5. The image processing apparatus according to claim 4, further comprising an output unit configured to output the information of the imaging state of the photoreceptor cells of the fundus image and/or the distribution information of the photoreceptor cells of the fundus image.

6. The image processing apparatus according to claim 5, wherein the output unit is configured to cause a display unit to display the fundus image and the information indicating the imaging state of the photoreceptor cells of the fundus image.

7. The image processing apparatus according to claim 6, wherein the information acquisition unit extracts the peak intensity value of the ring structure of the partial frequency image as the information indicating the imaging state of the photoreceptor cells of the fundus image.

8. The image processing apparatus according to claim 5, wherein the output unit is configure to cause a display unit to display the partial frequency image and/or the fundus image.

9. The image processing apparatus according to claim 1, wherein the fundus image of the eye is an image of the fundus of the eye obtained by focusing on a predetermined depth position of the fundus of the eye by a fundus imaging apparatus configured to correct an aberration by an aberration measurement unit and an adaptive optical system.

10. An image processing method for an image processing apparatus, the image processing method comprising:
    obtaining a fundus image of an eye;
    segmenting the fundus image into a plurality of partial images;
    obtaining a partial frequency image by performing frequency conversion for each of the plurality of partial images; and acquiring image quality information indicating an image quality of the fundus image based on at least one of the following:

an intensity value of a peak of a ring structure of the partial frequency image, a sharpness value that indicates a peak status of the ring structure, a position of the peak intensity value in the ring structure, a peak status and a position of a disk structure of the partial frequency image, and a peak intensity value in the disk structure, wherein acquiring further includes acquiring information about photoreceptor cells in each of the plurality of partial images.

11. The image processing method according to claim 10, wherein, in a case where information is acquired, acquiring includes extracting a blood vessel based on the acquired information.

12. The image processing method according to claim 10, wherein acquiring includes extracting a blood vessel based on the acquire information being information about the photoreceptor cells in each of the plurality of partial images.

13. The image processing method according to claim 10, wherein the acquired information includes at least one of the following: information of an imaging state of photoreceptor cells of the fundus image and/or distribution information of the photoreceptor cells of the fundus image.

14. The image processing method according to claim 13, further comprising outputting the information of the imaging state of the photoreceptor cells of the fundus image and/or the distribution information of the photoreceptor cells of the fundus image.

15. The image processing method according to claim 14, wherein outputting includes causing a display unit to display the fundus image and the information indicating the imaging state of the photoreceptor cells of the fundus image.

16. The image processing method according to claim 15, wherein acquiring includes extracting the peak intensity value of the ring structure of the partial frequency image as the information indicating the imaging state of the photoreceptor cells of the fundus image.

17. The image processing method according to claim 14, wherein outputting includes causing a display unit to display the partial frequency image and/or the fundus image.

18. The image processing method according to claim 10, wherein the fundus image of the eye is an image of the fundus of the eye obtained by focusing on a predetermined depth position of the fundus of the eye by a fundus imaging apparatus configured to correct an aberration by an aberration measurement unit and an adaptive optical system.

19. A non-transitory computer-readable storage medium storing a program to cause a computer to perform an image processing method for an image processing apparatus, the image processing method comprising:

obtaining a fundus image of an eye;

segmenting the fundus image into a plurality of partial images;

obtaining a partial frequency image by performing frequency conversion for each of the plurality of partial images; and acquiring image quality information indicating an image quality of the fundus image based on at least one of the following:

an intensity value of a peak of a ring structure of the partial frequency image, a sharpness value that indicates a peak status of the ring structure, a position of the peak intensity value in the ring structure, a peak status and a position of a disk structure of the partial frequency image, and a peak intensity value in the disk structure, wherein acquiring further includes acquiring information about photoreceptor cells in each of the plurality of partial images.

* * * * *